United States Patent
Man et al.

(10) Patent No.: US 11,492,332 B2
(45) Date of Patent: *Nov. 8, 2022

(54) ISOTOPOLOGUES OF 2-(TERT-BUTYLAM-INO)- 4-((1R,3R,4R)-3-HYDROXY-4-METHYLCYCLOHEXYLAMINO)-PYRIMIDINE-5-CARBOXAMIDE

(71) Applicant: Signal Pharmaceuticals, LLC, San Diego, CA (US)

(72) Inventors: Hon-Wah Man, Princeton, NJ (US); Mohit Atul Kothare, Bridgewater, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/195,814

(22) Filed: Mar. 9, 2021

(65) Prior Publication Data

US 2021/0221772 A1 Jul. 22, 2021

Related U.S. Application Data

(63) Continuation of application No. 16/871,143, filed on May 11, 2020, now Pat. No. 10,975,039, which is a continuation of application No. 16/452,691, filed on Jun. 26, 2019, now Pat. No. 10,689,351, which is a continuation of application No. 15/546,885, filed as application No. PCT/US2016/015276 on Jan. 28, 2016, now abandoned.

(60) Provisional application No. 62/109,096, filed on Jan. 29, 2015.

(51) Int. Cl.
*C07D 239/48* (2006.01)
*C07B 59/00* (2006.01)

(52) U.S. Cl.
CPC .......... *C07D 239/48* (2013.01); *C07B 59/002* (2013.01); *C07B 2200/05* (2013.01)

(58) Field of Classification Search
CPC ............................ C07D 239/48; A61K 31/505
USPC ........................................ 544/323; 514/275
See application file for complete search history.

(56) References Cited

U.S. PATENT DOCUMENTS

| | | | |
|---|---|---|---|
| 3,845,055 A | 10/1974 | Hoegerle et al. | |
| 6,221,335 B1 | 4/2001 | Foster et al. | |
| 6,417,360 B1 | 7/2002 | Breu et al. | |
| 6,432,963 B1 | 8/2002 | Hisamichi et al. | |
| 6,440,710 B1 | 8/2002 | Keinan et al. | |
| 6,603,008 B1 | 8/2003 | Ando et al. | |
| 7,169,798 B2 | 1/2007 | Green et al. | |
| 7,449,456 B2 | 11/2008 | Nagashima et al. | |
| 7,517,886 B2 | 4/2009 | Singh et al. | |
| 7,517,990 B2 | 4/2009 | Ito et al. | |
| 7,524,849 B2 | 4/2009 | Zhang | |
| 7,550,473 B2 | 6/2009 | Cardozo et al. | |
| 7,589,200 B2 | 9/2009 | Singh et al. | |
| 7,601,714 B2 | 10/2009 | Barbosa et al. | |
| 7,718,653 B2 | 5/2010 | Barlaam et al. | |
| 7,893,074 B2 | 2/2011 | Garcia/Echeverria et al. | |
| 7,956,060 B2 | 6/2011 | Arai et al. | |
| 8,338,439 B2 | 12/2012 | Sing et al. | |
| 8,513,242 B2 | 8/2013 | Chiang et al. | |
| 8,519,129 B2 | 8/2013 | Marsilje et al. | |
| 8,580,805 B2 | 11/2013 | Maehr | |
| 8,853,230 B2 | 10/2014 | Bauer et al. | |
| 8,969,336 B2 | 3/2015 | Shimada et al. | |
| 9,139,534 B2 | 9/2015 | Bennett et al. | |
| 9,365,524 B2 | 6/2016 | Man et al. | |
| 9,512,124 B2 | 12/2016 | Alexander et al. | |
| 9,513,297 B2 | 12/2016 | Horan et al. | |
| 9,701,643 B2 | 7/2017 | Bennett et al. | |
| 10,689,351 B2 | 6/2020 | Man et al. | |
| 10,975,039 B2 * | 4/2021 | Man ...................... | C07B 59/002 |
| 2007/0082929 A1 | 4/2007 | Gant et al. | |
| 2007/0197533 A1 | 8/2007 | Zhou et al. | |
| 2007/0197695 A1 | 8/2007 | Potyen et al. | |
| 2008/0139531 A1 | 6/2008 | Yanni et al. | |
| 2009/0036440 A1 | 2/2009 | Barlaam et al. | |
| 2011/0159019 A1 | 1/2011 | Tanaka et al. | |
| 2011/0130415 A1 | 6/2011 | Singh et al. | |
| 2013/0029987 A1 | 1/2013 | Bennett et al. | |
| 2016/0168105 A1 | 6/2016 | Boersen et al. | |
| 2017/0045531 A1 | 2/2017 | Horan et al. | |

FOREIGN PATENT DOCUMENTS

| | | |
|---|---|---|
| EP | 1 184 376 | 3/2002 |
| EP | 1 518 855 | 3/2005 |
| JP | 2006/1243 87 | 5/2006 |
| WO | WO 1999/31073 | 6/1993 |
| WO | WO 2000/12485 | 3/2000 |
| WO | WO 2000/76980 | 12/2000 |
| WO | WO 2003/063794 | 8/2003 |
| WO | WO 2003/078404 | 9/2003 |
| WO | WO 2003/082855 | 9/2003 |

(Continued)

OTHER PUBLICATIONS

Adeyeye, M. C. et al. (Eds.), *Preformulation in Solid Dosage Form Development*, CRC Press, 2008, pp. 239-240.

Bogoyevitch et al., 2010, "c-Jun N-temunal kinase (JNK) signaling: Recent advances and challenges," Biochimica et Biophysica Acta 1804:463-475.

Bosseray et al., PubMed Abstract (Pathol Biol (Paris) 50(8):483-92), Oct. 2002.

Bundgaard, "Design of prodrugs: Bioreversible derivatives for various functional groups and chemical entities," Design of Prodmgs, Chapter 1, p. 1, 1985.

Cohen P. 2001, "The role of protein phosphorylation in human health and disease." The Sir Hans Krebs Medal Lecture. Eur J Biochem. 268(19):5001-10.

(Continued)

*Primary Examiner* — Deepak R Rao
(74) *Attorney, Agent, or Firm* — Jones Day

(57) ABSTRACT

Provided herein are isotopologues of Compound A, which are enriched with isotopes such as, for example, deuterium. Pharmaceutical compositions comprising the isotope-enriched compounds, and methods of using such compounds are also provided.

12 Claims, No Drawings

(56) References Cited

FOREIGN PATENT DOCUMENTS

| WO | WO 2004/0143 82 | 2/2004 |
|---|---|---|
| WO | WO 2004/054617 | 7/2004 |
| WO | WO 2004/002964 | 8/2004 |
| WO | WO 2004/067516 | 8/2004 |
| WO | WO 2006/027377 | 3/2006 |
| WO | WO 2006/027378 | 3/2006 |
| WO | WO 2006/035069 | 4/2006 |
| WO | WO 2006/091737 | 8/2006 |
| WO | WO 2006/099231 | 9/2006 |
| WO | WO 2008/009458 | 1/2008 |
| WO | WO 2008/129380 | 10/2008 |
| WO | WO 2009/012421 | 1/2009 |
| WO | WO 2009/131687 | 10/2009 |
| WO | WO 2009/136995 | 11/2009 |
| WO | WO 2009/143389 | 11/2009 |
| WO | WO 2009/145856 | 12/2009 |
| WO | WO 2009/158571 | 12/2009 |
| WO | WO 2010/024430 | 3/2010 |
| WO | WO 2010/032875 | 3/2010 |
| WO | WO 2010/038081 | 4/2010 |
| WO | WO 2010/051223 | 5/2010 |
| WO | WO 2010/080864 | 7/2010 |
| WO | WO 2010/090875 | 8/2010 |
| WO | WO 2010/097248 | 9/2010 |
| WO | WO 2010/129802 | 11/2010 |
| WO | WO 2010/134533 | 11/2010 |
| WO | WO 2010/144468 | 12/2010 |
| WO | WO 2011/016472 | 2/2011 |
| WO | WO 2011/065800 | 6/2011 |
| WO | WO 2011/090760 | 7/2011 |
| WO | WO 2012/012619 | 1/2012 |
| WO | WO 2012/044936 | 4/2012 |
| WO | WO 2012/045010 | 4/2012 |
| WO | WO 2012/045020 | 4/2012 |
| WO | WO 2012/145569 | 10/2012 |
| WO | WO 2015/116755 | 8/2015 |
| WO | WO 2016/100308 | 6/2016 |
| WO | WO 2016/100310 | 6/2016 |
| WO | WO 2017/019487 | 2/2017 |

OTHER PUBLICATIONS

Cohen P. 2002, "Protein kinases—the major drug targets of the twenty-first century?" Nat Rev Drug Discov. 1(4):309-15.
Das et al., 1996, "Activation of raf-1, MEK, and MAP kinase in prolactin responsive mammary cells," Breast Cancer Res. Treat., 40(2):141-149.
Davis RJ., 1994, "MAPKs: new JNK expands the group." Trends Biochem Sci., 19(11):470-3.
Douglas, Jr., 1996, "Introduction to Viral Diseases," Cecil Textbook of Medicine, 20th Edition, vol. 2, pp. 1739-1747.
Eferl et al., 2008, "Development of pulmonary fibrosis through a pathway involving the transcription factor Fra-2/AP-1," PNAS, 105(30): 10525-10530.
Fanger et al., 1997, "MEKKs, GCKs, MLKs, PAKs, TAKs, and tpls: upstream regulators of the c-Jun amino-terminal kinases?" Curr Opin Genet Dev. 7(1):67-74.
Gaestel et al., 2007, "Protein kinases as small molecule inhibitor targets in inflammation." Curr Med Chem, 14(21):2214-34.
Goff, PubMed Abstract (J Gene Med 3(6):517-28), No.—Dec. 2001.
Grimminger et al., 2010, "Targeting non-malignant disorders with tyrosine kinase inhibitors," Nat Rev Drug Sisc., 9(12):956-970.
Hirabayashi et al., 2008, "A novel Syk family kinase inhibitor: design, synthesis, and structure-activity relationship of 1,2,4-triazolo[4,3-c]pyrimidine and 1,2,4-triazolo[1,5-c]pyrimidine derivatives," Bioorg Med Chem., 16:7347-7357.
Hirosumi et al., 2002, "A central role for JNK in obesity and insulin resistance," Nature, 420:333-336.
Hisamichi et al., 2005, "Corrigendum to Synthetic studies on novel Syk inhibitors. Part 1: Synthesis and structure -activity relationships of pyrimidine-5-carboxamide derivatives," Bioorg. Med. Chem., 13:6277-6279.

Hisamichi et al., 2005, "Synthetic studies on novel Syk inhibitors. Part 1: Synthesis and structure-activity relationships of pyrimidine-5-carboxamide derivatives," Bioorg Med Chem., 13:4936-4951.
Hu et al., 2000, "Prolonged activation of the mitogen-activated protein kinase pathway is required for macrophage-like differentiation of a human myeloid leukemic cell line," Cell Growth Differ., 11(4):191-200.
Hulikal, "L15 Deuterium Labeled Compounds in Dmg Discovery Process," Abstract, 2010.
Ichijo H., 1999, "From receptors to stress-activated MAP kinases." Oncogene. 18(45):6087-93.
Jones et al., 2012, Phase 1 Results From a Study of Romidepsin in Combination With Gemcitabine in Patients With Advanced Solid Tumors, Cancer Investigation, 30:481-486.
Kaneto et al., 2007, "Oxidative stress and the JNK pathway are involved in the development of type 1 and type 2 diabetes," Curr Mol Med., 7:674-686.
Katayama et al., 2008. "Identification of a key element for hydrogen-bonding patterns between protein kinases and their inhibitors," Proteins, 73:795-801.
Kluwe et al., 2010, "Modulation of hepatic fibrosis by c-Jun-N-terminal kinase inhibition," Gastroenterology 138:347-359.
Kodama et al., 2009, "c-Jun N-terminal kinase-1 from hematopoietic cells mediates progression from hepatic steatosis to steatohepatitis and fibrosis in mice," Gastroenterology, 137:1467-1477.e5.
Kyriakis JM., 2000, "MAP kinases and the regulation of nuclear receptors." Sci STKE. (48):pe1.
Le Jeune et al., 2006, "Evaluation of imatinib mesylate effects on glioblastoma aggressiveness with SPECT radiotracer 99mTc-(v)-DMSA." Eur J Cancer. 42(8):1004-13.
Liddle et al., 2011, "Discovery of GSK143, a highly potent, selective and orallv efficacious spleen tyrosine kinase inhibitor," Bioorg Chem Chem Lett., 21:6188-6194.
Malhi et al., 2006, "Free fatty acids induce JNK-dependent hepatocyte lipoapoptosis," J Biol Chem., 281:12093-12101.
Malhi et al., 2008, "Molecular mechanisms of lipotoxicity in nonalcoholic fatty liver disease," Semin Liver Dis., 28(4):360-369.
Nagashima et al., 2007, "Synthesis and evaluation of 2-{[2-(4-hydroxyphenyl)-ethyl]amino}pyrimidine-5-carboxamide derivatives as novel STAT6 inhibitors," Bioorg Med Chem., 15:1044-1055.
Nagashima et al., 2008, "Identification of 4-benzylamino-2-[(4-morpholin-4-ylphenyl)amino]pyrimidine-5-carboxamide derivatives as potent and orally bioavailable STAT6 inhibitors," Biorg Med Chem., 16:6509-6521.
Nagashima et al., 2009, "Novel 7H-pyrrolo[2,3-d]pyrimidine derivatives as potent and orally active STAT6 inhibitors," Bioorg Med Chem., 17:6926-6936.
Ohga et al., 2008, "YM-341619 suppresses the differentiation of spleen T cells into Th2 cells in vitro, eosinophilia, and airway hvperresponsiveness in rat allergic models," Eur J Pharmacol., 590:409-416.
Papp et al., 2007, "Steady state kinetics of spleen tyrosine kinase investigated by a real time fluorescence assay," Biochemistry, 46:15103-15114.
Pimlott, 2005, "Radiotracer development in psychiatry," PubMed Abstract (Nucl Med Commun. 26(3):183-188).
Razonable et al., PubMed Abstract (Herpes 10(3):60-5), Dec. 2003.
Reilly et al., 2011, "PRT-060318, a novel Syk inhibitor, prevents heparin-induced thrombocytopenia and thrombosis in a transgenic mouse model," Blood, 117(7):2241-2246.
Sanam et al., 2009, "Discovery of potential ZAP-70 kinase inhibitors: pharmacophore design. database screening and docking studies," Eur J Med Chem., 44:4793-4800.
Sanchez-Tillo et al., 2007, "JNK1 Is required for the induction of Mkpl expression in macrophages during proliferation and lipopolysaccharide-dependent activation," J Biol Chem., 282(17):12566-73.
Schramek H., 2002, "MAP kinases: from intracellular signals to physiology and disease." News Physiol Sci. 17:62-7.
Schwabe et al., 2004, "Differential requirement for c-Jun NH2-terminal kinase in TNF-α- and Fas-mediated apoptosis in hepatocytes," FASEB J, 18(6):720-722.

(56) References Cited

OTHER PUBLICATIONS

Seger and Krebs, 1995, "The MAPK signaling cascade." FASEB J. 9(9):726-35.
Silverman, 1992, "Prodrugs and Drug Delivery Systems," The Organic Chemistry of Drug Design and Drug action, Chapter 8, pp. 352-400.
Singh et al., 2009, "Differential effects of JNK1 and JNK2 inhibition on murine steatohepatitis and insulin resistance." Hepatology, 49(1):87-96.
Singh et al.. 2012, "Discovery and development of spleen tyrosine kinase (SYK) inhibitors," J Med Chem., 55:3614-1643.
Sridhar et al., 2000, "Protein kinases as therapeutic targets," Pharm Res., 17(11):1345-1353.
Storey, R. A et al. (Eds.), *Solid State Characterization of Pharmaceuticals*, Wiley-Blackwell, 2011, pp. 473-491, 490.
Uehara et al., 2004, "c-Jun N-Terminal Kinase Mediates Hepatic Injury after Rat Liver Transplantation," Transplantation, 78(3):324-332.
Vallerie et al., 2010, "The role of JNK proteins in metabolism," Sci Transl Med., 2(60):1 -7.
Villasenor et al.. 2009, "Structural insights for design of potent spleen tyrosine kinase inhibitors from crystallographic analysis of three inhibitor complexes," Chem Biol Drug Des., 73:466-470.
Virkamaki et al., 1999. "Protein-protein interaction in insulin signaling and the molecular mechanisms of insulin resistance," J Clin Invest, 103 (7):931-943.
Whitmarsh AJ, et al. 1999, "Signal transduction by MAP kinases: regulation bv phosphorylation-dependent switches." Sci. STKE. (1):pe1.
Xie et al., 2009, "Pharmacophore modeling study based on known spleen tyrosine kinase inhibitors together with virtual screening for identifying novel inhibitors," Bioorg Med Chem Lett., 19:1944-1949.
Alcorn et al., 2009, "c-Jun N-Terminal Kinase 1 Is Required for the Development of Pulmonary Fibrosis". Am. J. Respir. Cell. Mol, Biol., vol. 40: 422-432.
Davis., 2000, "Signal Transduction by the JNK Group of MAP Kinases", Cell, vol. 103: 239-252.
Lee et al.. 2005, "Bleomycin induces alveolar epithelial cell death through JNK-dependent activation of the mitochondrial death pathway", Am. J. Physiol. Lung Cell. Mol, Physiol., 289: L521-L528.
Lin et al., 2013, "Connective tissue growth factor induces collagen I expression in human lung fibroblasts through the Rac1/MLK3/JNK/AP-1 pathway", Biochimica et Biophysica Acta, 1833: 2823-2833.
Yoshida et al., 2002, "MAP kinase activation and apoptosis in lung tissues from patients with idiopathic pulmonary fibrosis", J. Pathol., 198: 388-396.
Dyck et al., (1986) "Effects of Deuterium Substitution on the Catabolism of β-Phenylethylamine: An In Vivo Study," Journal of neurochemistry, 46.2 (1986): 399-404.
Foster et al., (1985) "Deuterium isotope effects in the metabolism of drugs andxenobiotics: implications for drug desing," *Advanes in Drug Research* 14 (1985): 1-40.
Fukuto et al., (1991) "Determination of the mechanism of demethylenation of (methylenedioxy) phenyl compounds by cytochrome P450 using deuterium isotope effects," *Journal of medicinal chemistry*, 34.9 (1991): 2871-2876.
Fisher et al., (2006) "The Complexities Inherent in Attempts to Decrease Dmg Clearance by Blocking Sites of CYP-Mediated Metabolism," *Current Opinion in Drug Discovery & Development*, vol. 9, pp. 101-109 (2006).
Tonn, (1993). Biological Mass Spectrometry vol. 22 Issue 11, pp. 633-642 (1993).
Haskins, (1982), Biomedical Spectrometry vol. 9 Issue 7, pp. 269-277 (1982).
Walen, (1986,) Journal of Clinical Pharmacology (1986); 26:419-424.
Browne, (1998), Journal of Clinical Pharmacology (1998); 38:213-220.
Baillie, (1981), Pharmacology' Rev.(1981); 33:81-132.
Gouyette, (1988), Biomedical And Environmental Mass Spectrometry, vol. 15. 243-247 (1988).
Cherrah, (1987), Biomedical and Environmental Mass Spectrometry vol. 14 Issue 11. pp. 653-657 ( 1987).
Pieniaszck, (1999), J Clin Pharmacol.(1999); 39:817-825.
Honma et al., (1987), Drug Metab Dispos 15 (4): 551-559 (1987).
Pearce et al., (2008), Failure modes in anticancer dmg discovery' and development, Cancer Drag Design and Discovery' Edited by Stephen Neidle, Chapter 18, pp. 424-435 (2008).
Johnson et al., (2001), Relationships between drag activity in NCI preclinical in vitro and in vivo models and early clinical trials, British Journal of Cancer, 84(10): 1424-1431, 2001.
Gura et al., (1997), Systems for identifying new drags are often faulty, Science, 278: 1041-1042, 1997.
Simone, (1996), Oncology: Introduction, Cecil Textbook of Medicine, 20th Edition, vol. 1, pp. 1004-1010, 1996.
Ulrich, (2002), Crystallization, Kirk-Othmer Encyclopedia of Chemical Technology, pp. 1-7, 2002.
Vippagunta et al.. (2001), Crystalline Solids, Advanced Drug Delivery Reviews 48 (2001), pp. 3-26.
O'Driscoll, (2009) "Heavyweight drugs," Chemistry & Industry, Society Of Chemical Industry', London, GB, Mar. 9, 2009, pp. 24-26, XP002636700.
Concert Pharmaceuticals, (2007) "Precision Deuterium Chemistry Backgrounder," Internet Citation, 2007, pp. 1-6, XP002636701.
Buteau KC. (2009) "Deuterated Drugs: Unexpectedly Nonobvious?," Journal Of High Technology Law, vol. X, No. 1 Jan. 1, 2009, pp. 22-74, XP002636702.
Fisher et al., (2006) "The Complexities Inherent in Attempts to Decrease Drag Clearance by Blocking Sites of CYP-Mediated Metabolism," *Current Opinion in Drug Discovery & Development*, vol. 9, pp. 101-109 (2006).

* cited by examiner

ISOTOPOLOGUES OF 2-(TERT-BUTYLAMINO)-4-((1R,3R,4R)-3-HYDROXY-4-METHYLCYCLOHEXYLAMINO)-PYRIMIDINE-5-CARBOXAMIDE

This application is a continuation of U.S. application Ser. No. 16/871,143, filed May 11, 2020, currently allowed, which is a continuation of U.S. application Ser. No. 16/452,691, filed Jun. 26, 2019, issued as U.S. Pat. No. 10,689,351 on Jun. 23, 2020, which is a continuation of U.S. application Ser. No. 15/546,885, filed Jul. 27, 2017, which is a U.S. national stage application of International Patent Application No. PCT/US2016/015276, filed Jan. 28, 2016, which claims the benefit of U.S. Provisional Application No. 62/109,096, filed Jan. 29, 2015, the entire content of which is incorporated herein by reference.

1 FIELD

Provided herein are isotopologues of certain heterocyclic carboxamides, compositions comprising the isotopologues, methods of making the isotopologues, and methods of their use for treatment or prevention of diseases and conditions including, but not limited to, inflammatory diseases, autoimmune diseases, and cancers.

2 BACKGROUND

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.* 14: 2214-223 (2007); Grimminger et al. *Nat. Rev. Drug Disc.* 9(12):956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

JNK is a ubiquitously expressed serine/threonine kinase belonging, together with ERK (extracellular-regulated kinase) and p38, to the family of mitogen-activated protein kinases (MAPKs). (Kyriakis J M, *Sci. STKE* (48):pel (2000); Whitmarsh A J, et al. *Sci. STKE* (1):pel (1999); Schramek H, *News Physiol. Sci.* 17:62-7 (2002); Ichijo H, *Oncogene* 18(45):6087-93 (1999)). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. (Davis R J, *Trends Biochem. Sci.* 9(11):470-473 (1994); Seger R et al., *FASEB* J; 9(9):726-35 (1995); Fanger G R et al., *Curr. Opin. Genet. Dev.;* 7(1):67-74 (1997)).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways.

The compound chemically named 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide) and tautomers thereof are disclosed in U.S. Patent Application Publication No. 2013/0029987, published on Jan. 31, 2013, and International Pub. No. WO2012/145569, the entireties of each of which are incorporated by reference herein.

Citation or identification of any reference in Section 2 of this application is not to be construed as an admission that the reference is prior art to the present application.

3 SUMMARY

Embodiments provided herein encompass isotopologues of Compound 1:

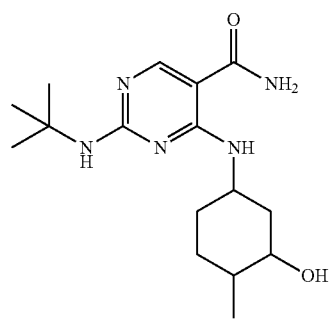

I and pharmaceutically acceptable salts, stereoisomers, tautomers, solid forms, polymorphs, hydrates, clathrates, and solvates thereof (collectively with Compound 1 referred to herein as "Compound A"). In one embodiment, Compound 1 is 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide).

In certain embodiments, the isotopologue is an isotopologe of the following structure:

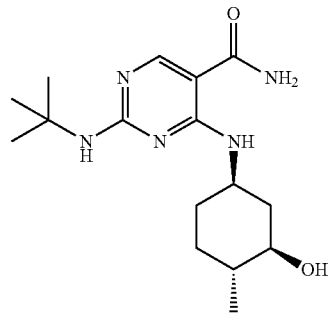 [SMILES: C[C@@H]1CC[C@@H](Nc2nc(NC(C)(C)C)ncc2C(N)=O)C[C@H]1O]

Certain embodiments encompass mixtures of an isotopologue of Compound A. Certain embodiments encompass methods of synthesizing, isolating, or characterizing an isotopologue of Compound A. In certain embodiments, the isotopologues of Compound A are deuterium, carbon-13, nitrogen-15, or oxygen-18 enriched, or combinations thereof.

Further provided herein are methods for using the pharmaceutical compositions and dosage forms of an isotopologue of Compound A for treating or preventing diseases or disorders treatable or preventable by inhibition of a JNK pathway, as described herein. In some embodiments, the diseases or disorders include, but are not limited to, interstitial pulmonary fibrosis, systemic sclerosis, scleroderma, chronic allograft nephropathy, antibody mediated rejection, or lupus. In other embodiments, the diseases or disorders include, but are not limited to, liver fibrotic disorders, or diabetes and/or metabolic syndrome leading to liver fibrotic disorders, as described herein.

The present embodiments can be understood more fully by reference to the detailed description and examples, which are intended to exemplify non-limiting embodiments.

4 DETAILED DESCRIPTION

The descriptions of the terminology provided below apply to the terms as used herein, unless otherwise specified.

The term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

The term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, about 0.0156% of molecules in a sample synthesized using non-enriched starting materials will have deuterium at a given position.

The term "isotopic enrichment factor" refers to the ratio between the isotopic composition and the natural isotopic composition of a specified isotope.

It should also be noted that an isotopologue of Compound A can contain unnatural proportions of atomic isotopes at one or more of the atoms. For example, an isotopologue of Compound A may be radiolabeled at one more positions with radioactive isotopes, such as for example tritium ($^3H$), and/or carbon-14 ($^{14}C$), or may be isotopically enriched at one or more positions, such as with deuterium ($^2H$), carbon-13 ($^{13}C$), oxygen-18 ($^{18}O$) and/or nitrogen-15 ($^{15}N$). In certain embodiments, Compound A can be radiolabeled at one more positions with radioactive isotopes, such as for example tritium ($^3H$), and/or carbon-14 ($^{14}C$), while also being isotopically enriched at one or more positions, such as with deuterium ($^2H$), carbon-13 ($^{13}C$), oxygen-18 ($^{18}O$) and/or nitrogen-15 ($^{15}N$).

The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of Compound A, whether radioactive or not, are intended to be encompassed within the scope of the embodiments provided herein. In some embodiments, there are provided isotopologues of Compound A, for example, the isotopologues are deuterium, carbon-13, or nitrogen-15 enriched Compound A.

With regard to the compounds provided herein, when a particular atomic position is designated as having deuterium or "D," it is understood that the abundance of deuterium at that position is substantially greater than the natural abundance of deuterium, which is about 0.0156%. A position designated as having deuterium typically has a minimum isotopic enrichment factor of, in particular embodiments, at least 100 (1.56% deuterium incorporation), at least 500 (7.8% deuterium incorporation), at least 1000 (15.6% deuterium incorporation), at least 2000 (31.2% deuterium incorporation), at least 3000 (46.8% deuterium incorporation), at least 3500 (54.6% deuterium incorporation), at least 4000 (62.4% deuterium incorporation), at least 4500 (70.2% deuterium incorporation), at least 5000 (78% deuterium incorporation), at least 5500 (85.8% deuterium incorporation), at least 6000 (93.6% deuterium incorporation), at least 6089.7 (95% deuterium incorporation), at least 6217.9 (97% deuterium incorporation), at least 6346.2 (99% deuterium incorporation), or at least 6378.2 (99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, L-asparate, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. Compounds can have chiral centers and can occur as racemates, individual enantiomers or diastereomers, and mixtures thereof. All such isomeric forms are included within the embodiments disclosed herein, including mixtures thereof. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds can include E and Z isomers, or a mixture thereof, and cis and trans isomers or a mixture thereof. In certain embodiments, compounds are isolated as either the cis or trans isomer. In other embodiments, compounds are a mixture of the cis and trans isomers.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, a crystalline that is "pure," i.e., substantially free of other crystalline or amorphous solids, contains less than about 10% by weight of one or more other crystalline or amorphous solids, less than about 5% by weight of one or more other crystalline or amorphous solids, less than about 3% by weight of one or more other crystalline or amorphous solids, or less than about 1% by weight of one or more other crystalline or amorphous solids.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

As readily understood by one skilled in the art, a wide variety of functional groups and other structures may exhibit tautomerism and all tautomers of the isotopologues of Compound A are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

"JNK" means a protein or an isoform thereof expressed by a JNK1, JNK2, or JNK3 gene (Gupta, S., Barrett, T., Whitmarsh, A. J., Cavanagh, J., Sluss, H. K., Derijard, B. and Davis, R. J. *The EMBO J.*, Vol. 15, pp. 2760-70 (1996)).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In yet another embodiment, the disorder is a liver fibrotic disorder, or diabetes and/or metabolic syndrome leading to liver fibrotic disorders, as described herein. In some embodiments, the disorder is a liver fibrotic disorder, such as non-alcoholic steatohepatitis, steatosis (i.e., fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g., viral infection such as HCV), with liver transplant, or with drug induced liver injury (e.g., acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e., fatty liver), hepatitis or cirrhosis, or a slowing, or halting of further progression or worsening of those symptoms. In one embodiment, the symptom is jaundice.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In one embodiment, the disorder is a liver fibrotic disorder, or diabetes or metabolic syndrome leading to liver fibrotic disorders, as described herein, or symptoms thereof.

The term "effective amount" in connection with an isotopologue of Compound A means an amount capable of treating or preventing a disorder, disease or condition, or symptoms thereof, disclosed herein.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for having interstitial pulmonary fibrosis, systemic sclerosis, scleroderma, chronic allograft nephropathy, antibody mediated rejection, or lupus. In another, a subject is a human having or at risk for having liver fibrotic disorders or diabetes or metabolic syndrome leading to liver fibrotic disorders, or a condition, treatable or preventable by inhibition of a JNK pathway, or a symptom thereof. In one embodiment, a subject is fasted. In another embodiment, a subject is fed.

4.1 Compounds

Provided herein are isotopically enriched compounds, including isotopically enriched Compound A and synthetic intermediates thereof.

Isotopic enrichment (e.g., deuteration) of pharmaceuticals to improve pharmacokinetics ("PK"), pharmacodynamics ("PD"), and toxicity profiles has been demonstrated previously with some classes of drugs. (See, e.g., Lijinsky et. al., *Food Cosmet. Toxicol.*, Vol. 20, p. 393 (1982); Lijinsky et. al., *J. Nat. Cancer Inst.*, Vol. 69, p. 1127 (1982); Mangold et. al., *Mutation Res.* Vol. 308, p. 33 (1994); Gordon et. al., *Drug Metab. Dispos.*, Vol. 15, p. 589 (1987); Zello et. al., *Metabolism*, Vol. 43, p. 487 (1994); Gately et. al., *J. Nucl. Med.*, Vol. 27, p. 388 (1986); Wade D, *Chem. Biol. Interact.*, Vol. 117, p. 191 (1999)).

Without being limited by a particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction or an enzyme catalyzed reaction. This phenomenon is known as the Kinetic Isotope Effect ("KIE"). For example, if a C—H bond is broken during a rate-determining step in a chemical reaction (i.e., the step with the highest transition state energy), substitution of a deuterium for that hydrogen can cause a decrease in the reaction rate and the process may slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as T2O. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

In some embodiments, provided herein are deuterated analogues of Compound A, wherein one or more atomic positions of Compound A is/are isotopically enriched with deuterium. Certain embodiments herein provide compounds of the following structure of Compound A:

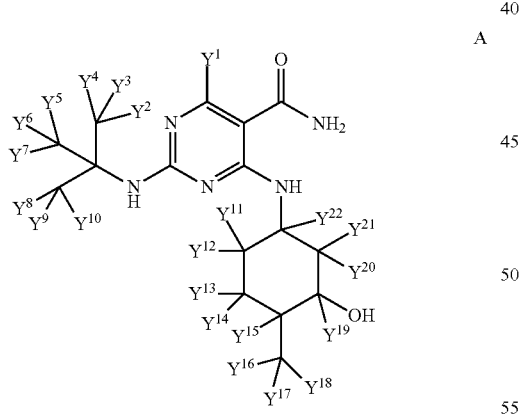

A wherein one or more Y atoms (i.e., $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, and $Y^{22}$) is/are hydrogen(s) isotopically enriched with deuterium, and any remaining Y atom(s) is/are non-enriched hydrogen atom(s). In particular embodiments, one, two, three, four, five, six, seven, eight or nine of the indicated Y atoms is/are isotopically enriched with deuterium, and any remaining Y atom(s) is/are non-enriched hydrogen(s). In one embodiment, all of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$, and $Y^{22}$ are isotopically enriched with deuterium.

In certain embodiments, one or more Y atoms on the cyclohexyl portion of Compound A is/are deuterium-enriched. For example, particular compounds provided herein include the following listed compounds, wherein the label "D" indicates a deuterium-enriched atomic position, i.e., a sample comprising the given compound has a deuterium enrichment at the indicated position(s) above the natural abundance of deuterium:

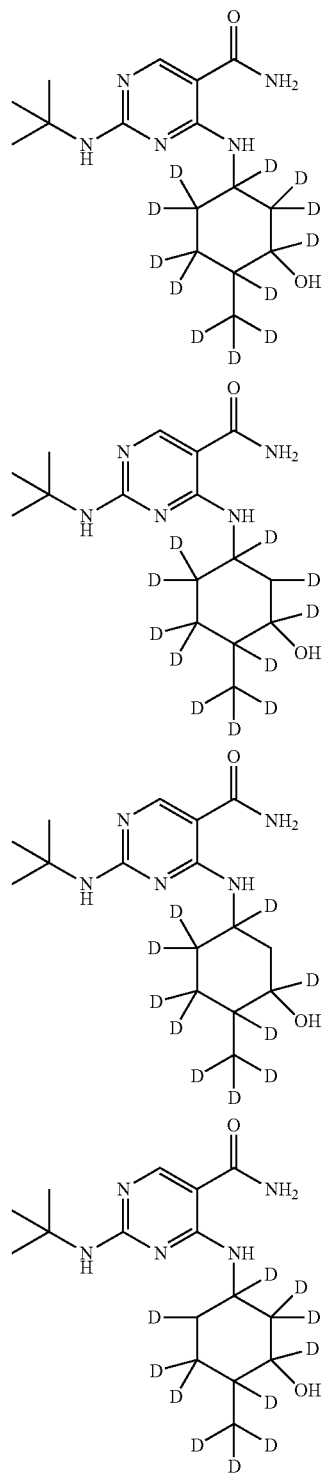

| 11 -continued | 12 -continued |
|---|---|
| 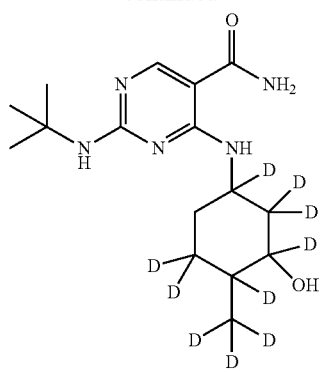 | 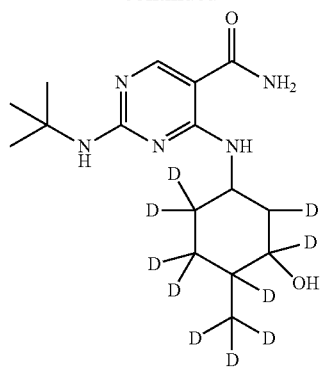 |
| 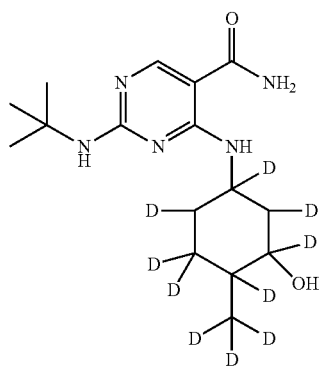 | 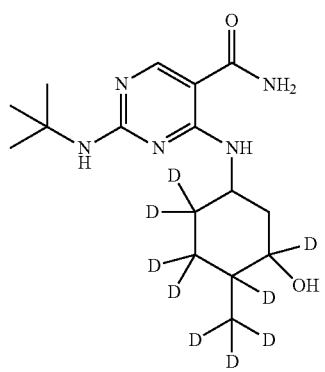 |
| 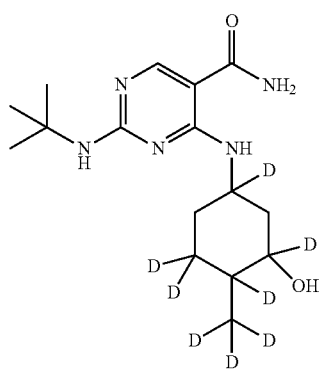 | 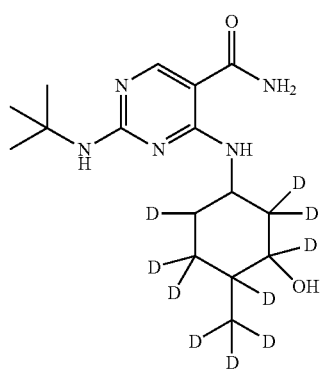 |
| 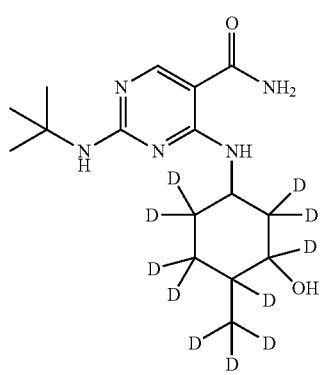 | 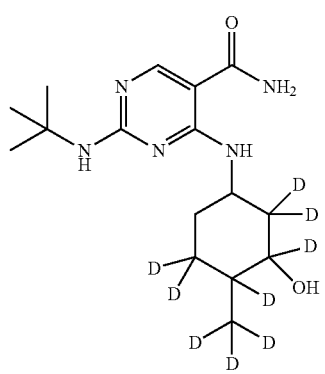 |

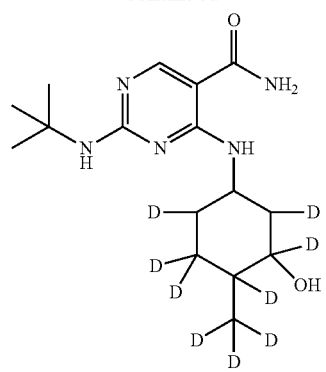
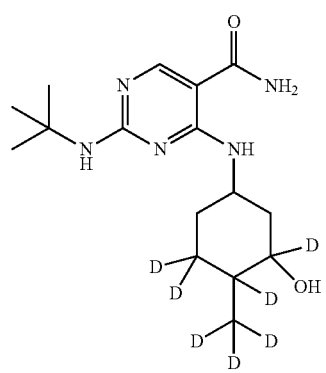
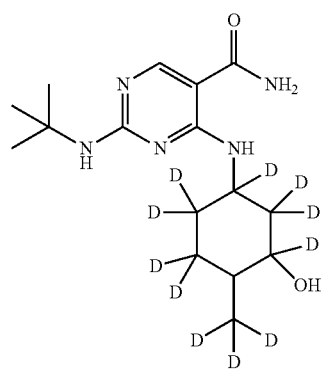
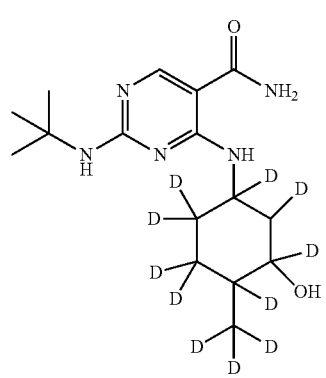
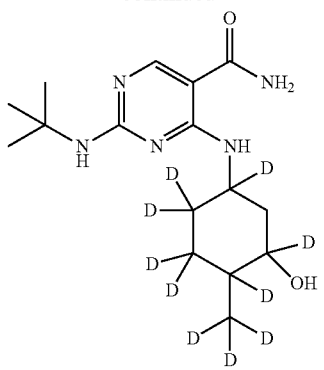
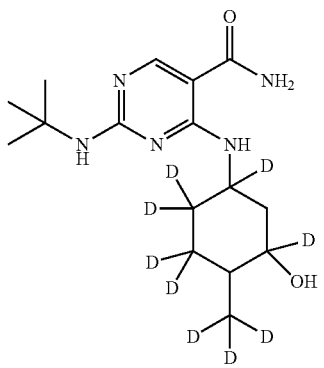
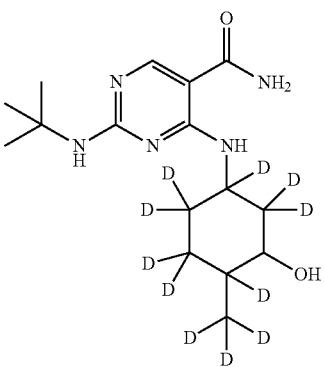
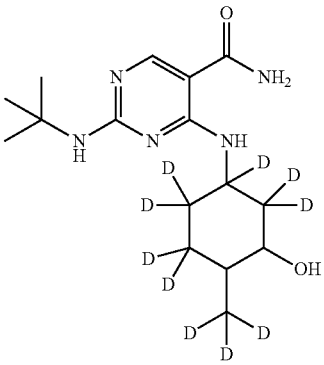

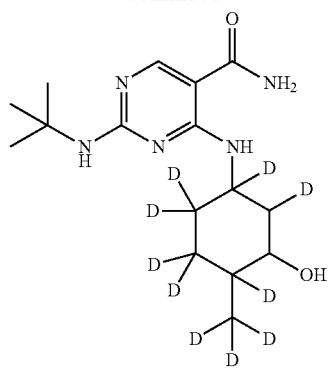
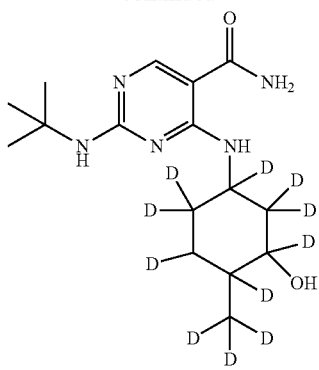
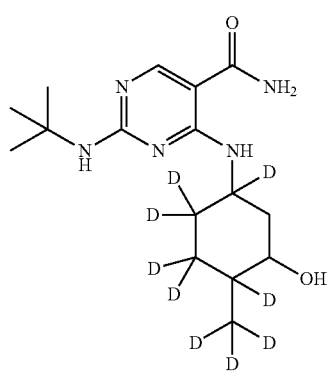
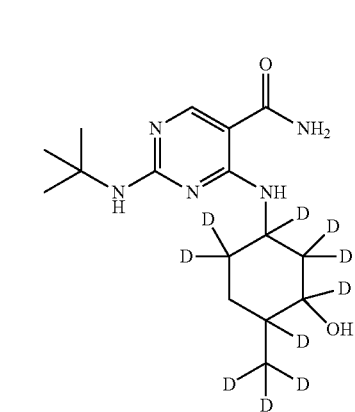
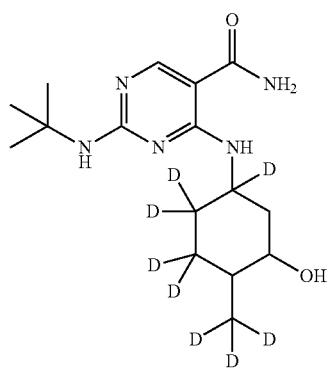
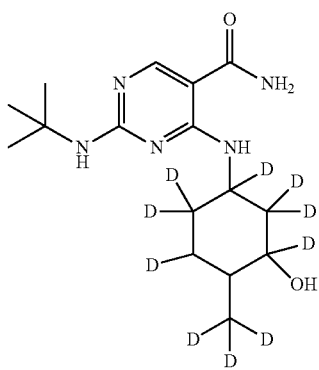
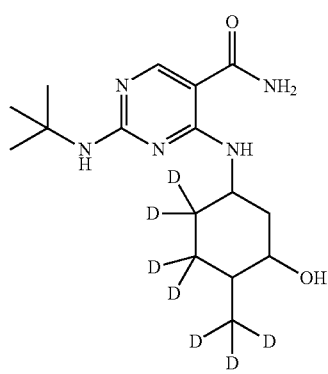
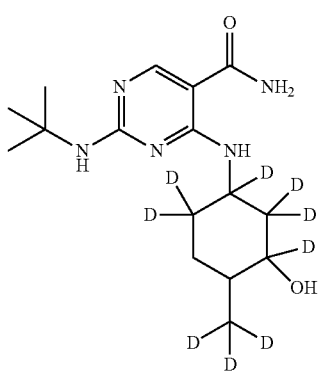

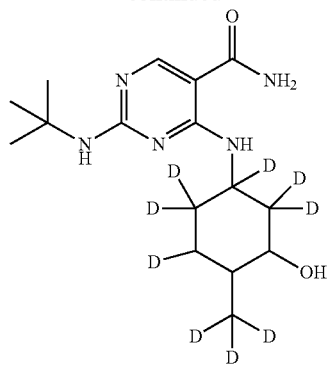
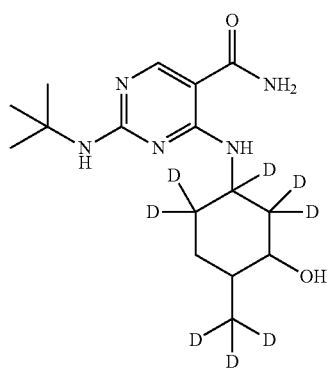
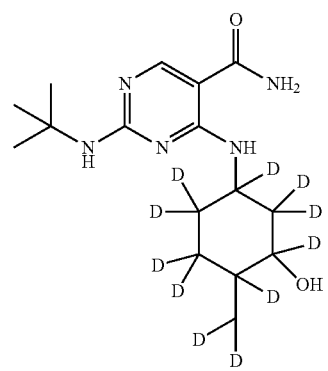
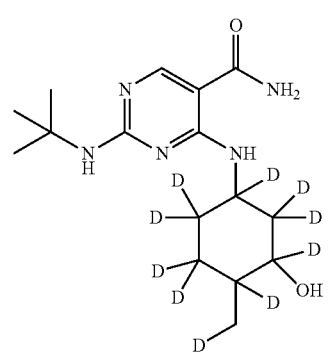
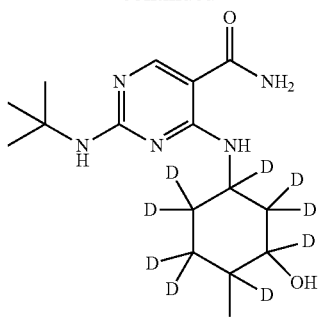
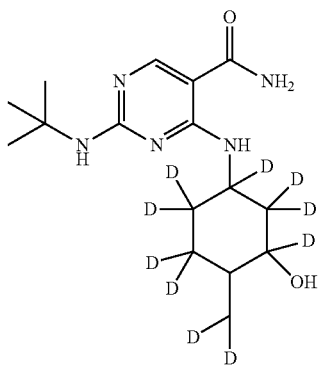
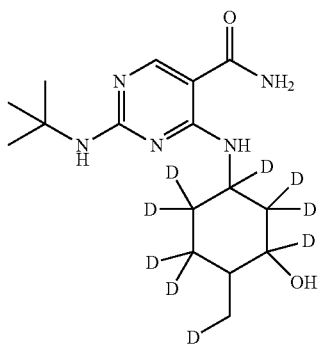
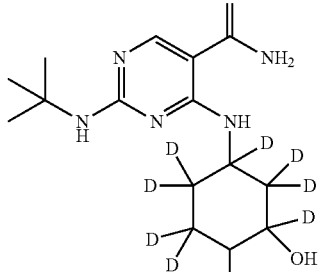
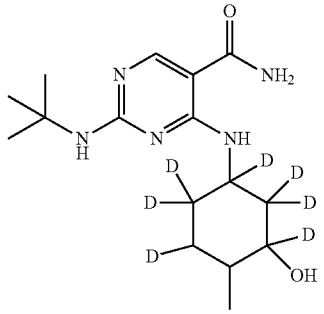

-continued
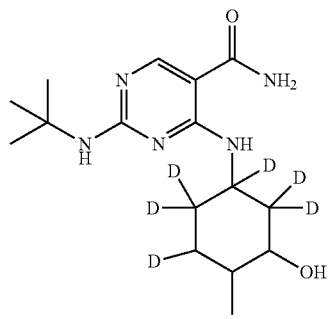
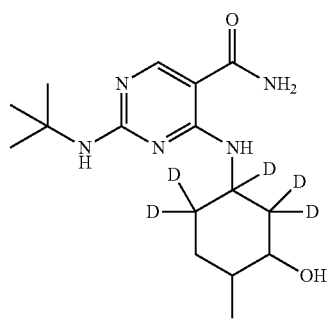
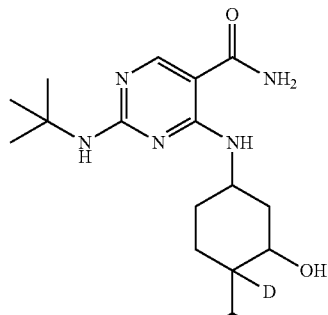
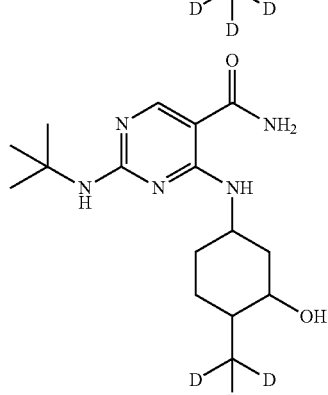
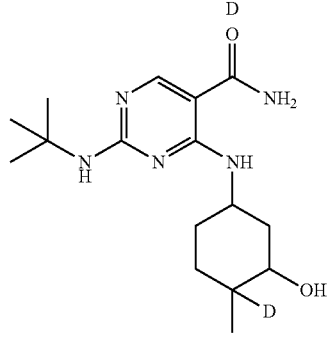
-continued
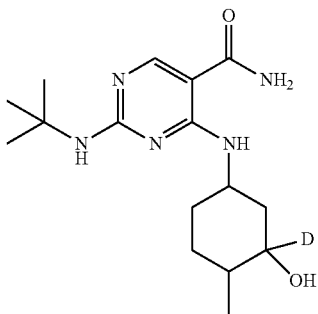
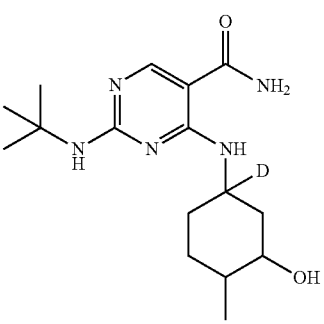
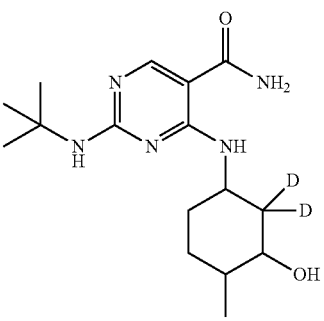
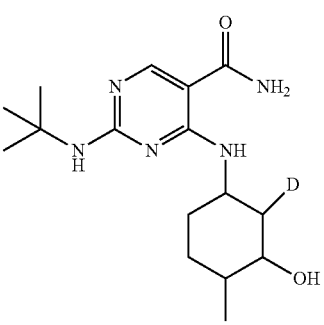
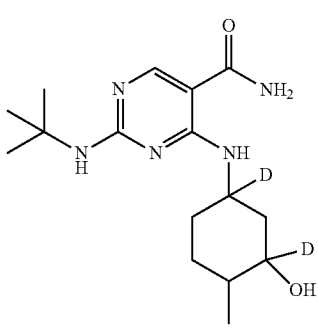

-continued
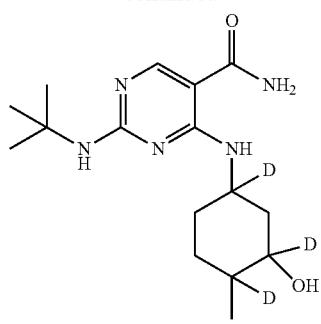
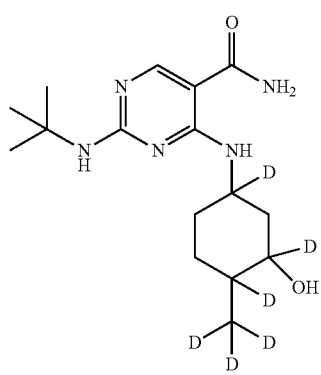
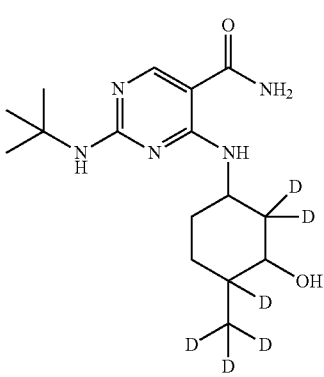
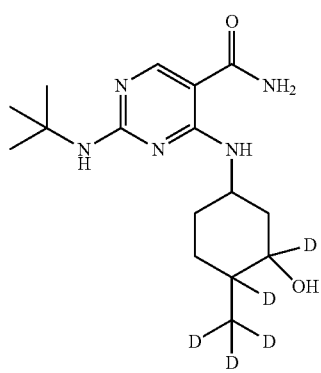
-continued
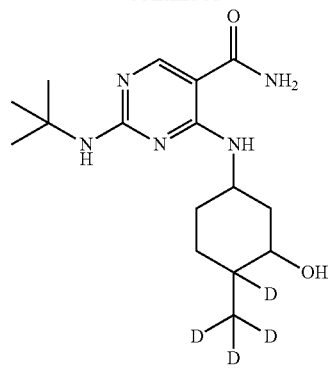
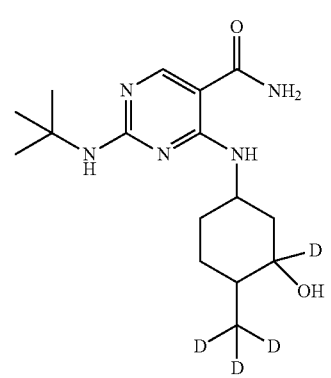
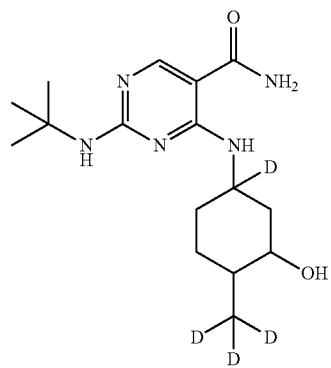
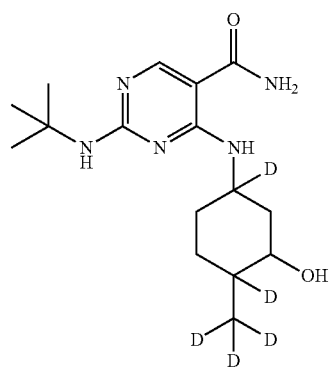

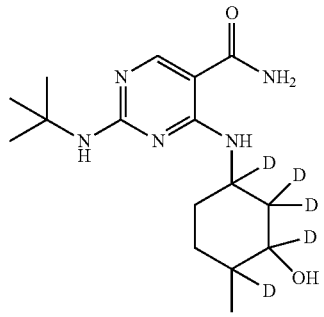
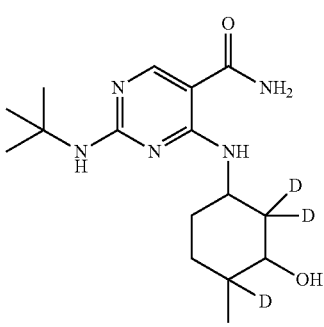
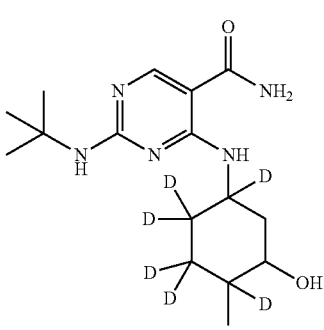
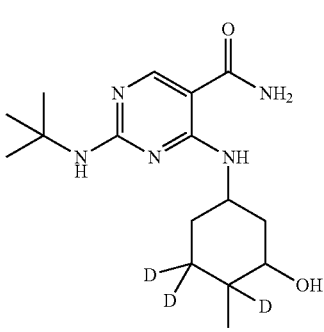
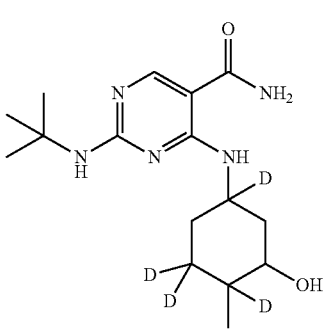
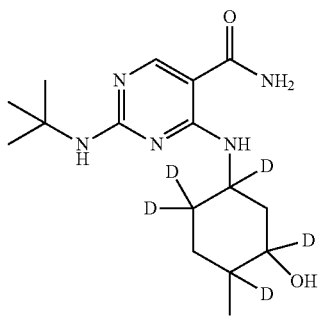
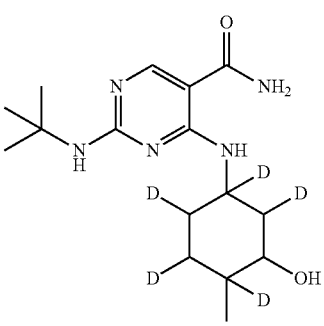
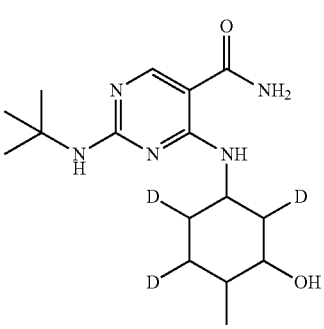
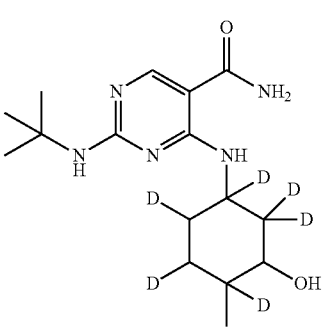
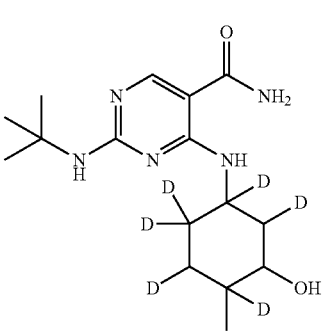

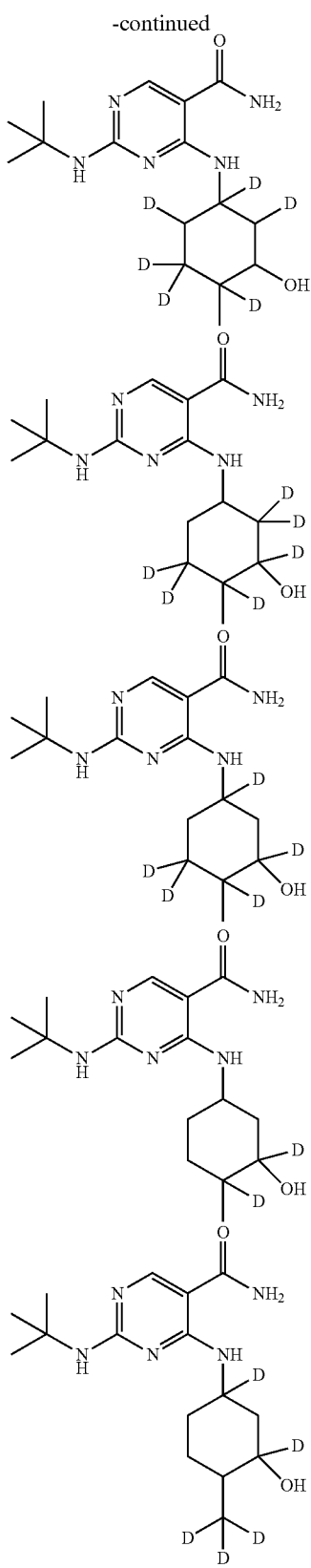

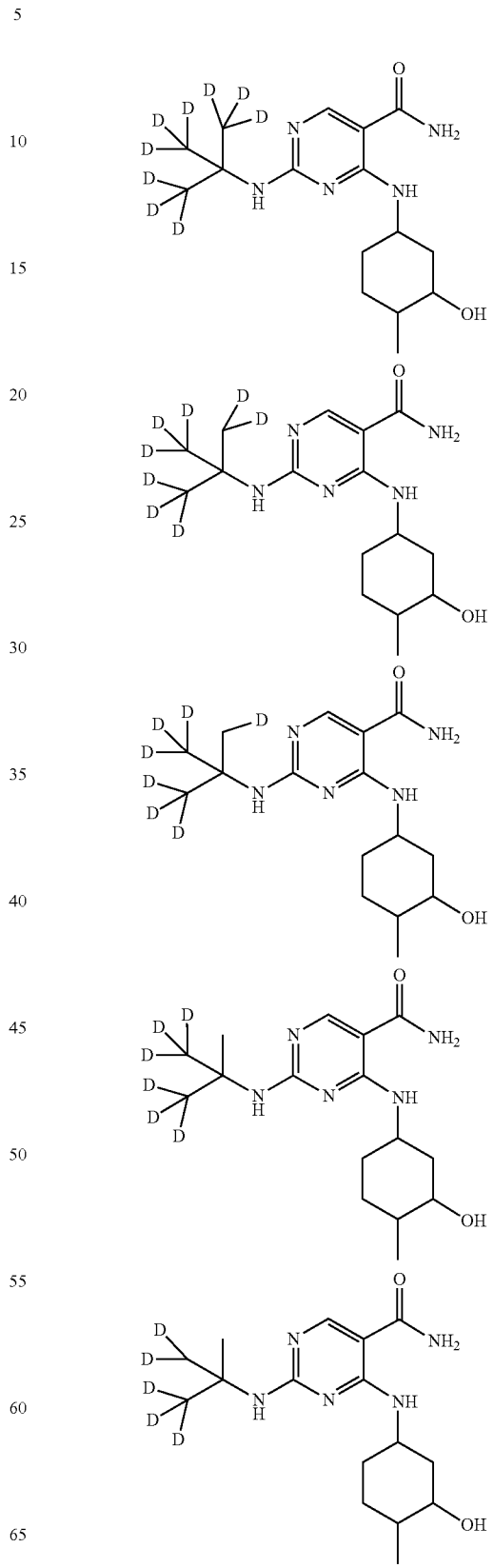

wherein the label "D" indicates a deuterium-enriched atomic position, i.e., a sample comprising the given compound has a deuterium enrichment at the indicated position(s) above the natural abundance of deuterium:

In certain embodiments, one or more Y atoms on the tert-butyl portion of Compound A are deuterium-enriched. For example, particular compounds provided herein include, but are not limited to, the following listed compounds, 27
-continued

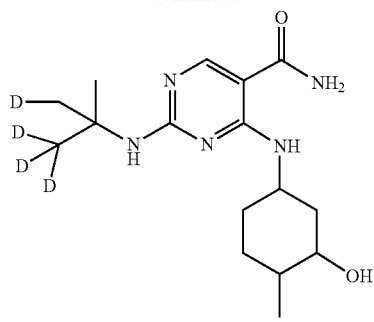

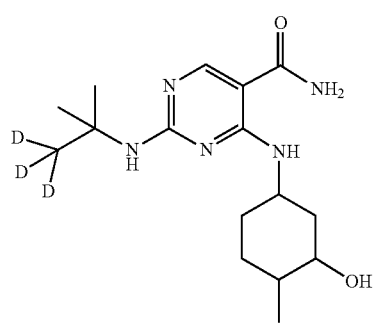

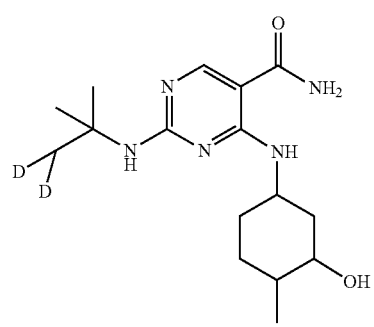

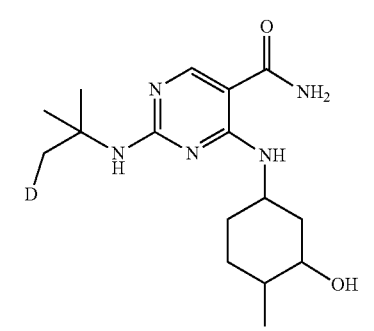

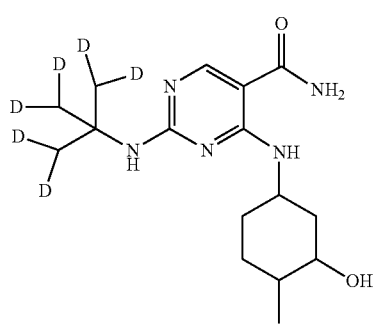

28
-continued

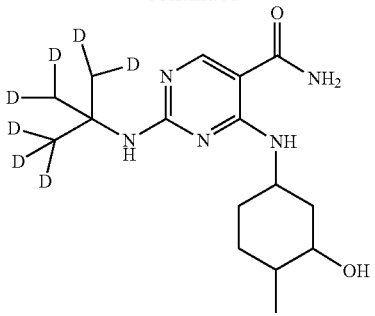 [SMILES: [2H]C([2H])C(Nc1ncc(C(N)=O)c(NC2CCC(C)C(O)C2)n1)(C([2H])[2H])C([2H])([2H])[2H]]

In certain embodiments, one or more Y atoms on the pyrimidine portion of Compound A is/are deuterium-enriched. For example, particular compounds provided herein include, but are not limited to, the following listed compounds, wherein the label "D" indicates a deuterium-enriched atomic position, i.e., a sample comprising the given compound has a deuterium enrichment at the indicated position(s) above the natural abundance of deuterium:

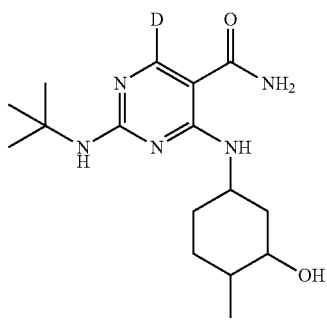 [SMILES: [2H]c1nc(NC(C)(C)C)nc(NC2CCC(C)C(O)C2)c1C(N)=O]

In certain embodiments, one or more Y atoms on the cyclohexyl, tert-butyl, and/or pyrimidine portions of Compound A is/are deuterium-enriched, i.e., any combination of deuteration enrichment shown above is encompassed. In some embodiments the compound is selected from:

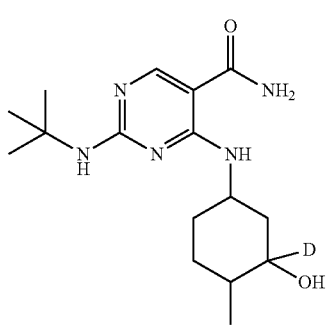

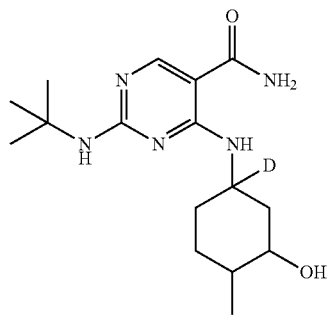
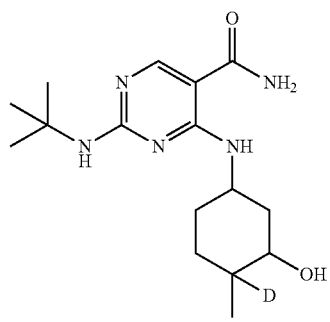
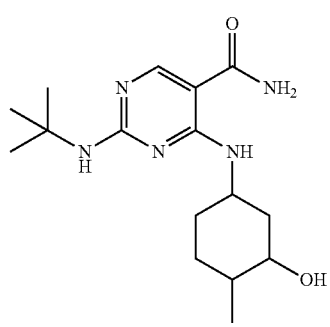
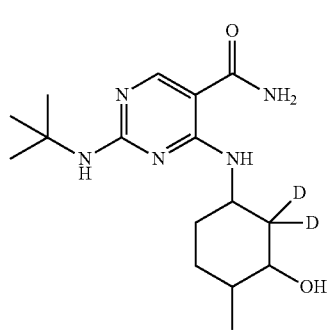
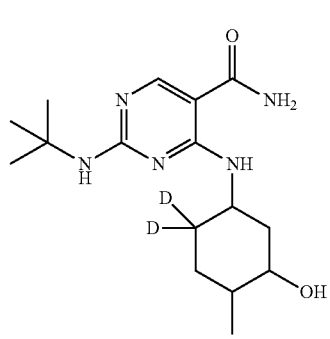
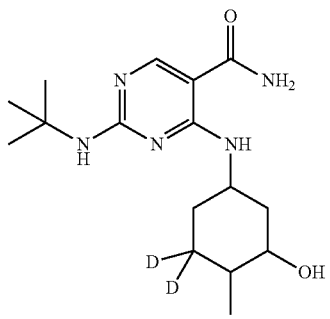
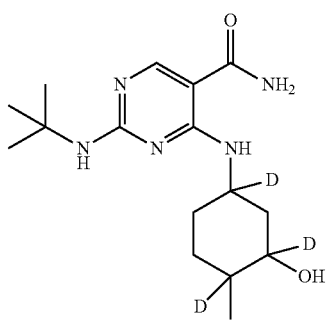
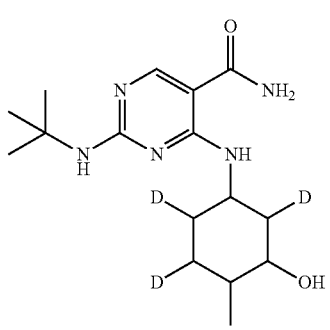
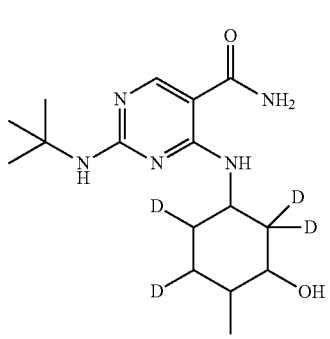
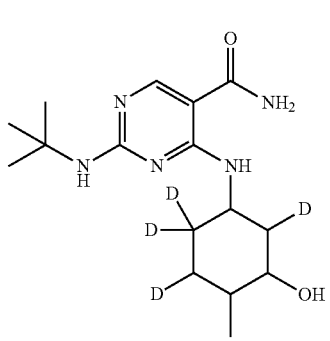

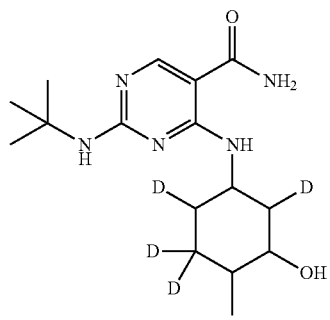
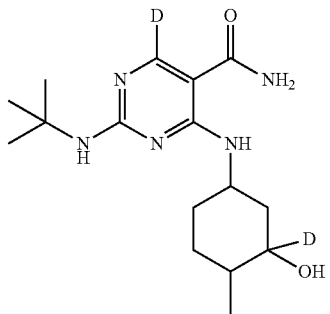
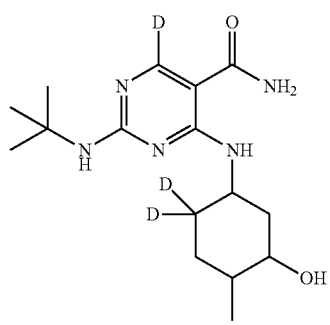
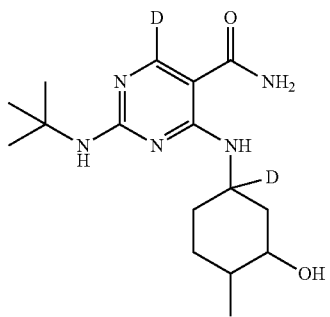
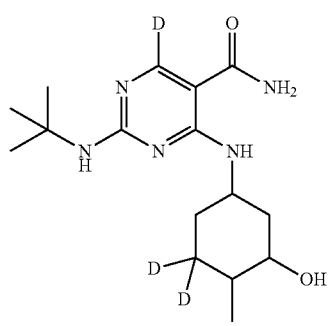
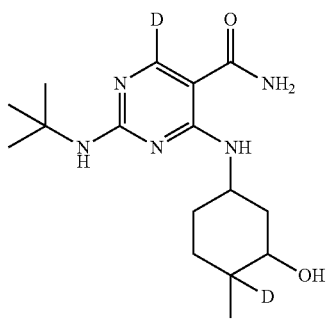
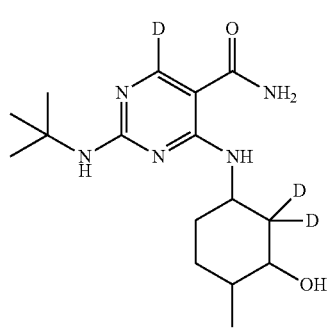
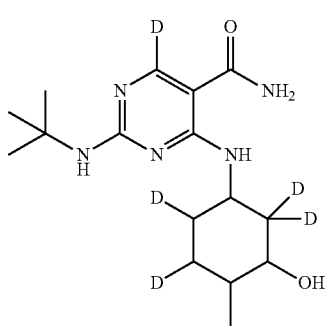
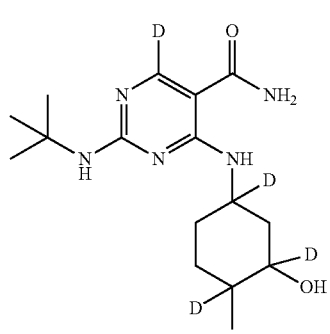
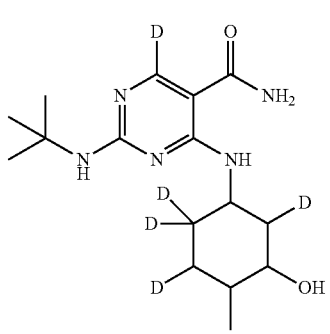

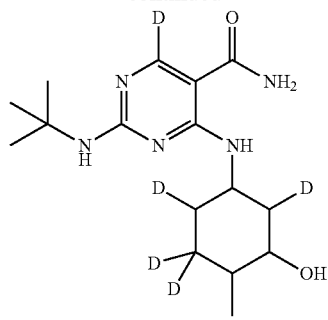
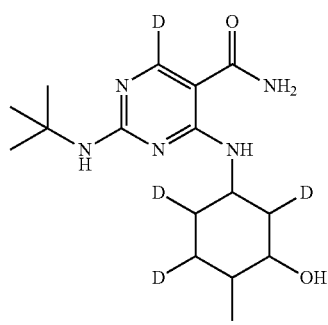
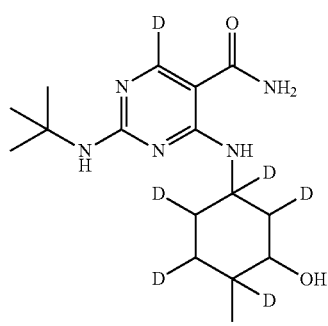
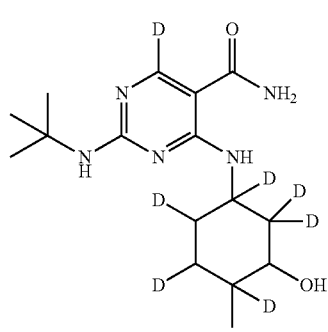
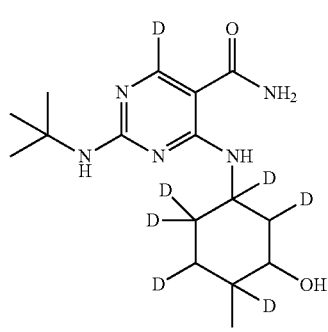
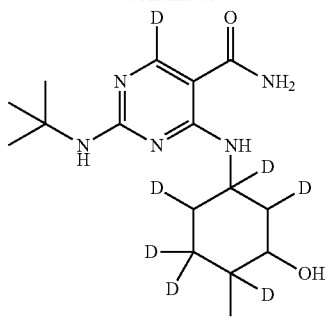
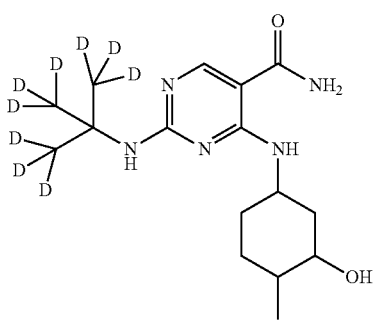
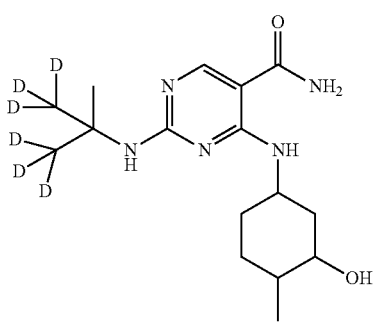
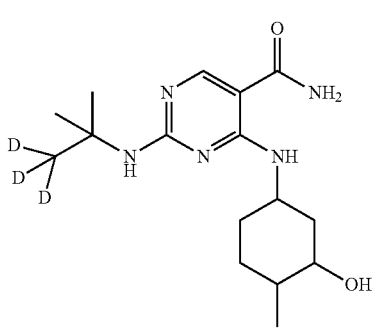
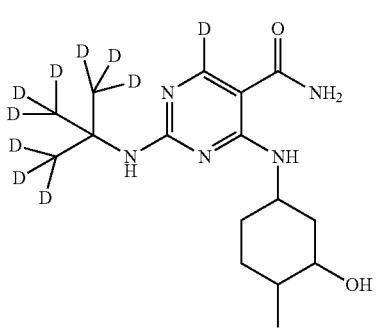

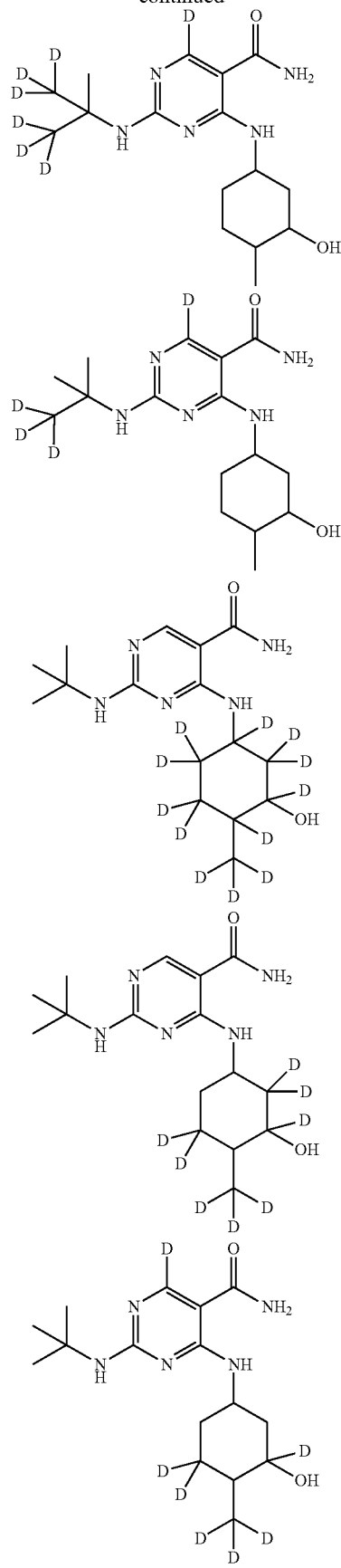
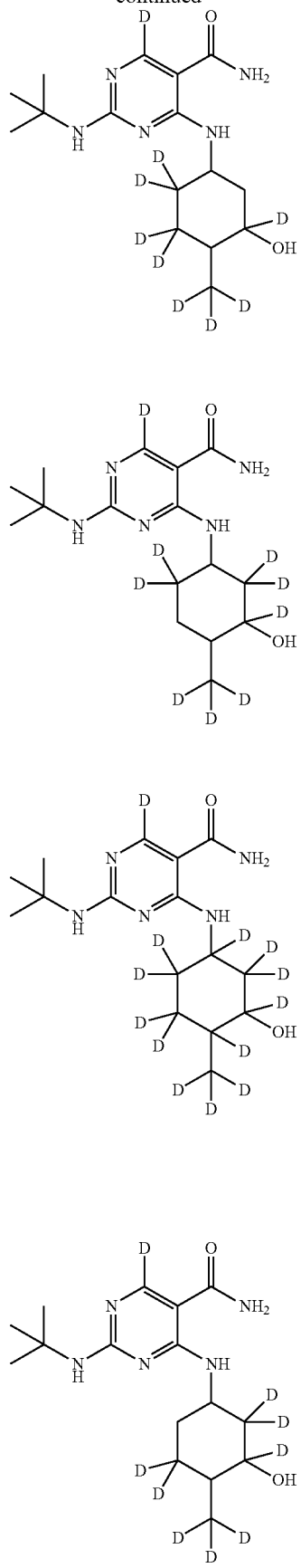

37
-continued
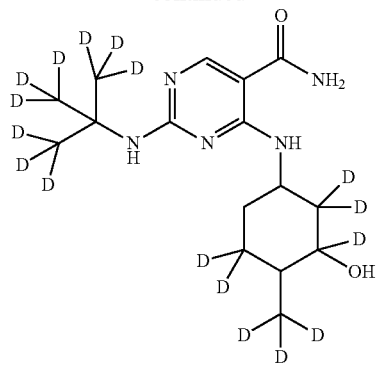
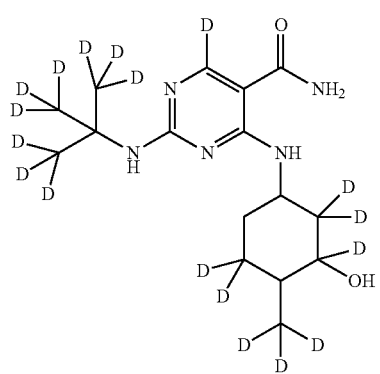
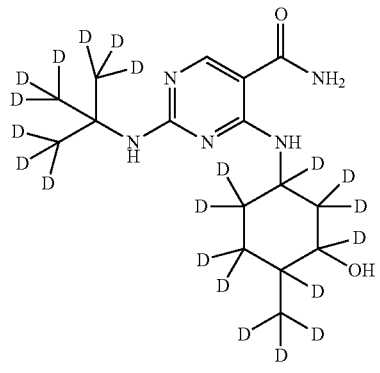
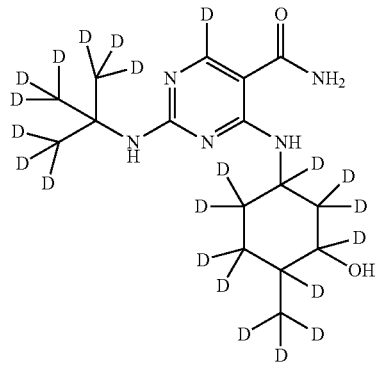
38
-continued
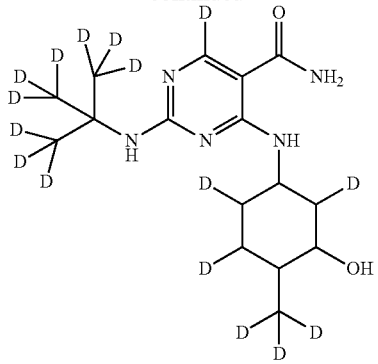
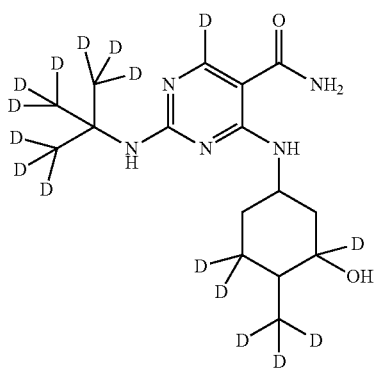
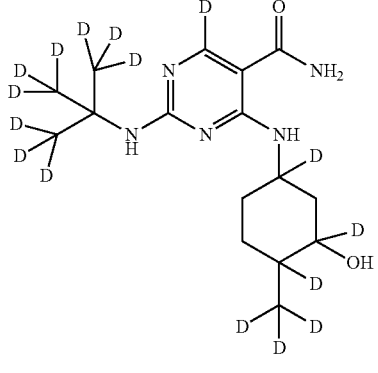
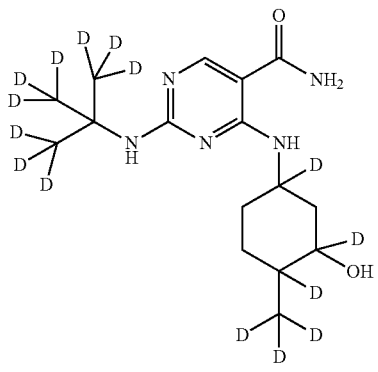

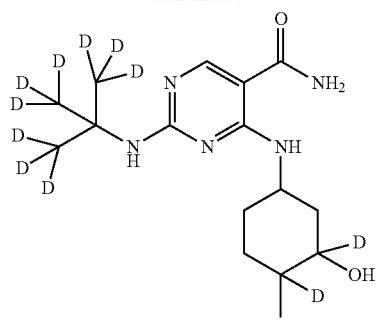
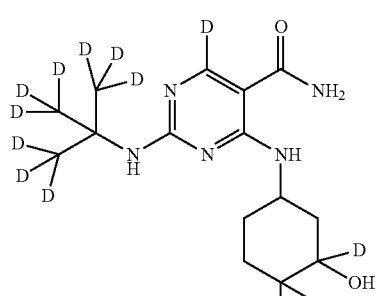
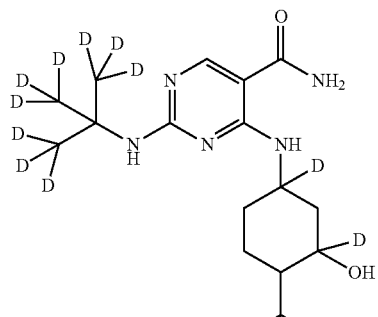
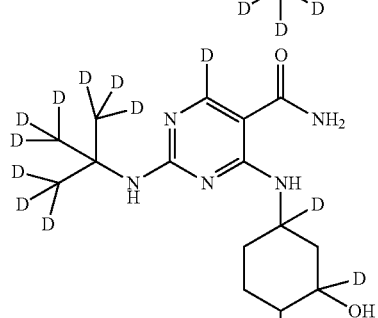
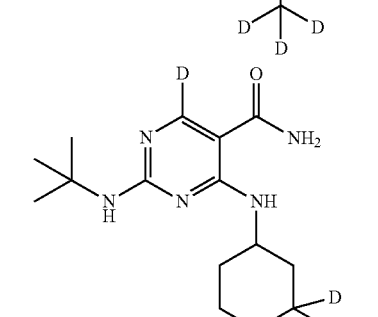
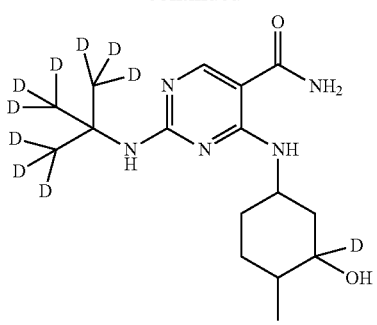
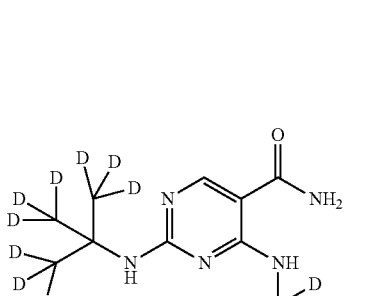
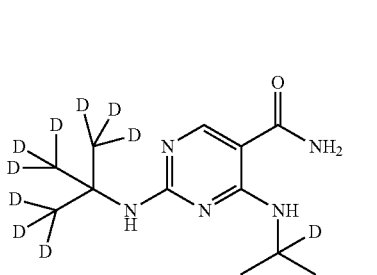
In one embodiment, the compound is
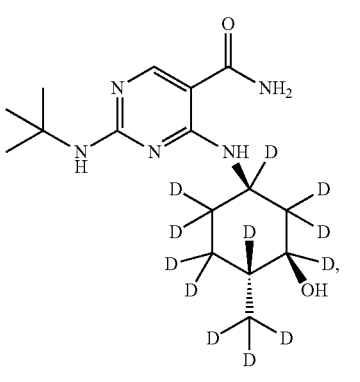

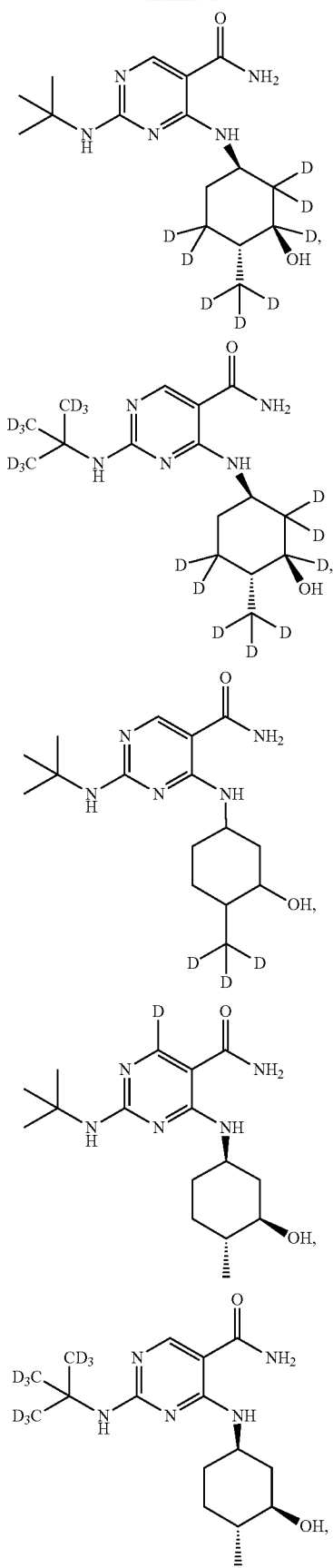
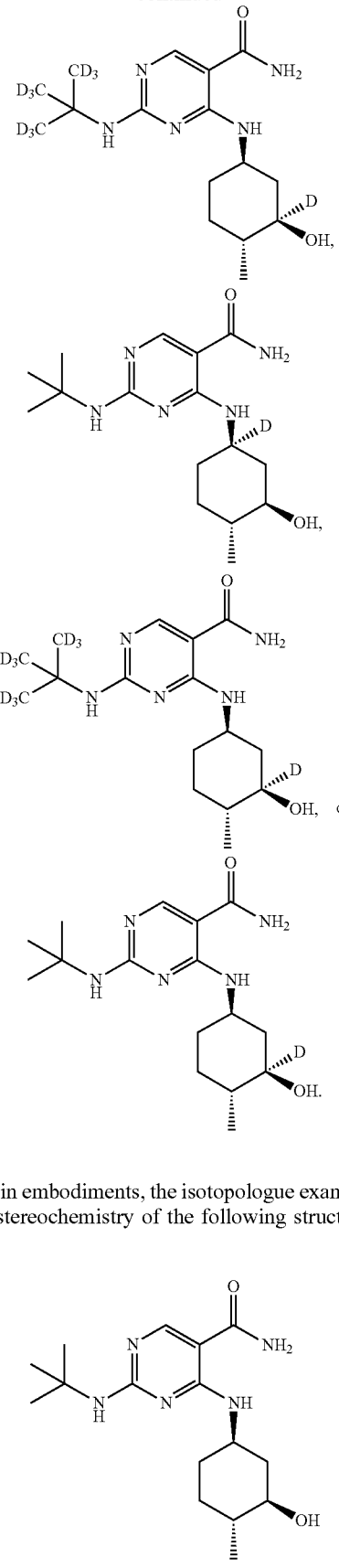
In certain embodiments, the isotopologue examples above have the stereochemistry of the following structure:
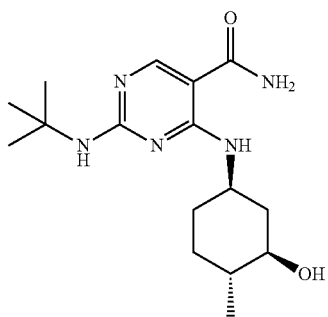 [SMILES: C[C@@H]1CC[C@@H](Nc2nc(NC(C)(C)C)ncc2C(N)=O)C[C@H]1O]

It is understood that one or more deuteriums may exchange with hydrogen under physiological conditions.

4.2 Synthesis

The compounds described herein may be synthesized using methods known to those of ordinary skill in the art. For example, particular compounds described herein are synthesized using standard synthetic organic chemistry techniques known to those of ordinary skill in the art.

In some embodiments, known procedures for the synthesis of Compound 1 are employed, wherein one or more of the reagents, starting materials, precursors, or intermediates are replaced by one or more isotopically-enriched reagents or intermediates, including but not limited to one or more deuterium-enriched reagents, starting materials, precursors, or intermediates. Such known procedures for the synthesis of Compound 1 and tautomers thereof include, but are not limited to, those described in U.S. Patent Application Publication No. 2013/0029987, published on Jan. 31, 2013, and International Pub. No. WO2012/145569, the entireties of each of which are incorporated by reference herein. Isotopically enriched reagents, starting materials, precursors, and intermediates are commercially available or may be prepared by routine chemical reactions known to one of skill in the art.

U.S. Patent Application Publication No. 2013/0029987 described procedures for synthesizing Compound 1 as shown in the Scheme 1 below.

In some embodiments, one or more hydrogen positions of the cyclohexyl, tert-butyl, and/or pyrimidine portions of Compound 1 are enriched with deuterium through organic synthesis. In some embodiments, the methods of Scheme 1 are employed.

In particular embodiments, the methods of Scheme 2 are employed, as depicted below:

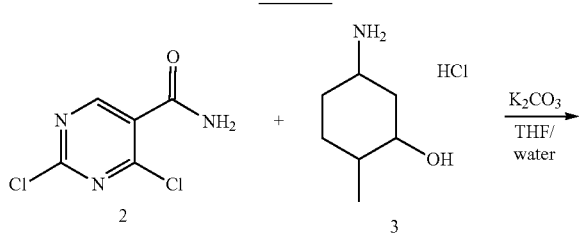

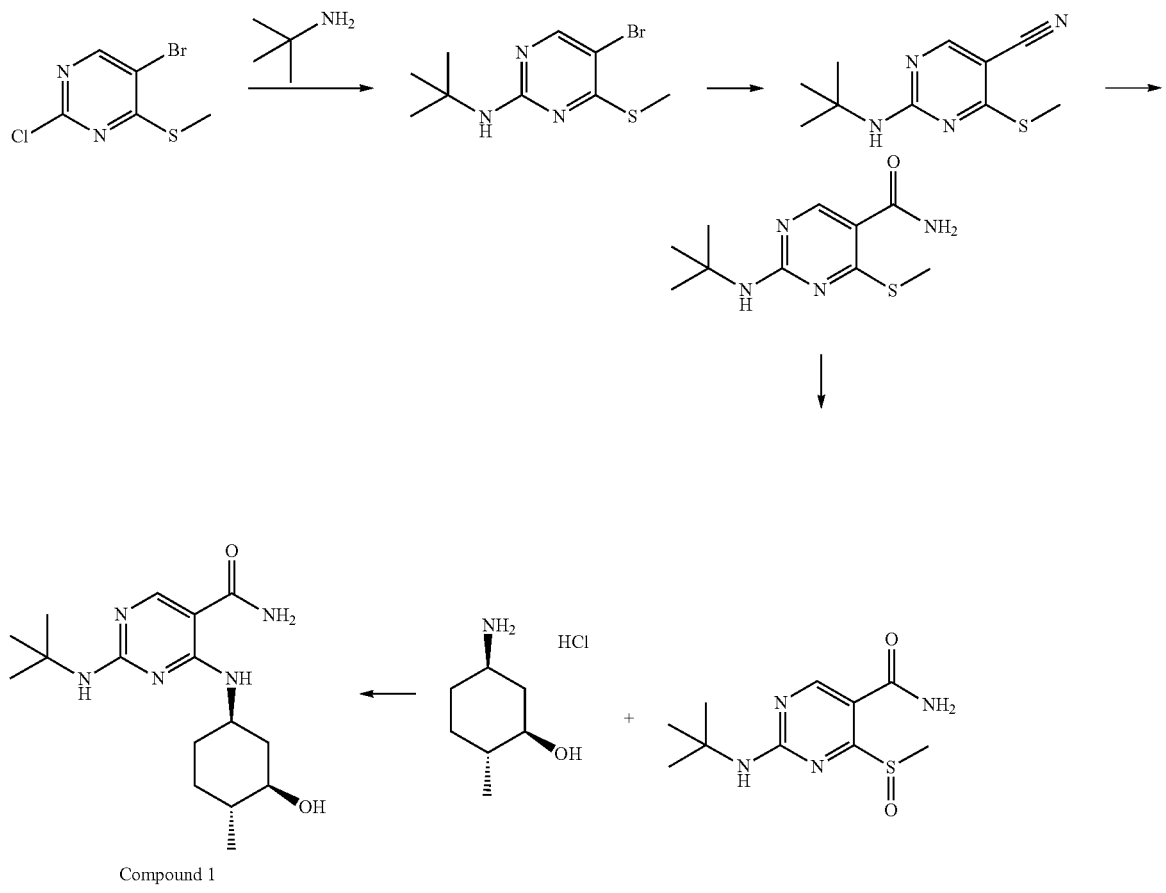

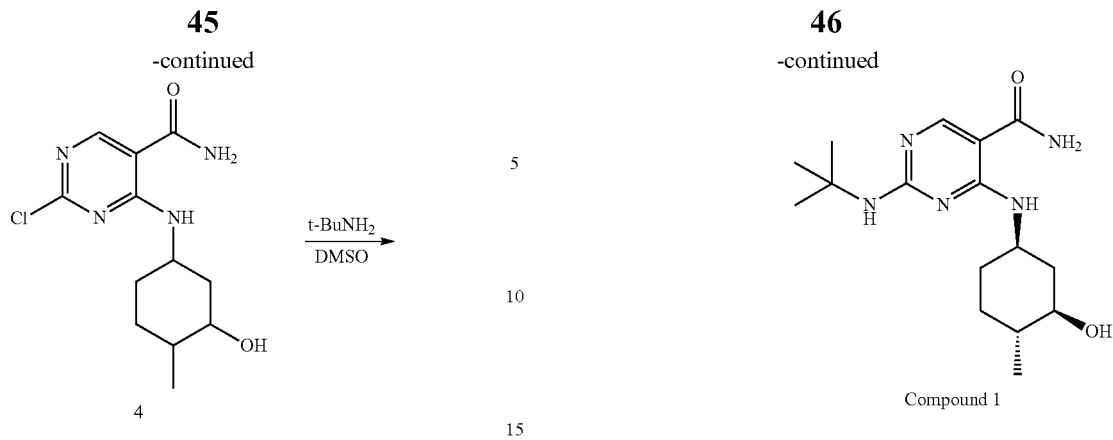

Compound 1

In certain embodiments, the methods of Scheme 2 have the stereochemistry as depicted below in Scheme 3:

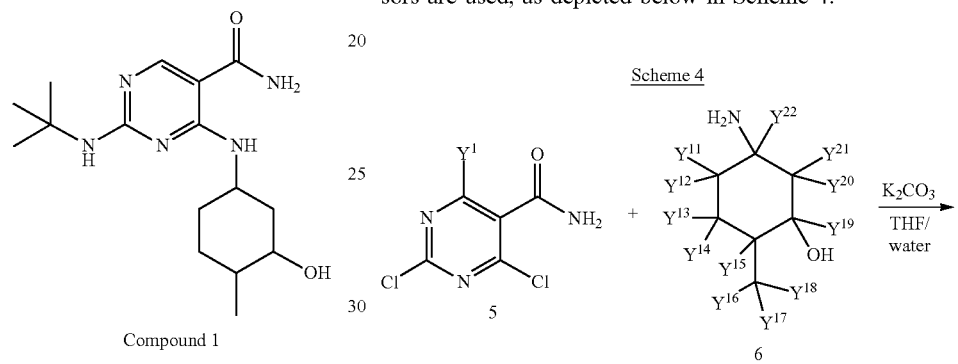

In some embodiments, the methods of Scheme 2 are employed, wherein one or more deuterium-enriched precursors are used, as depicted below in Scheme 4:

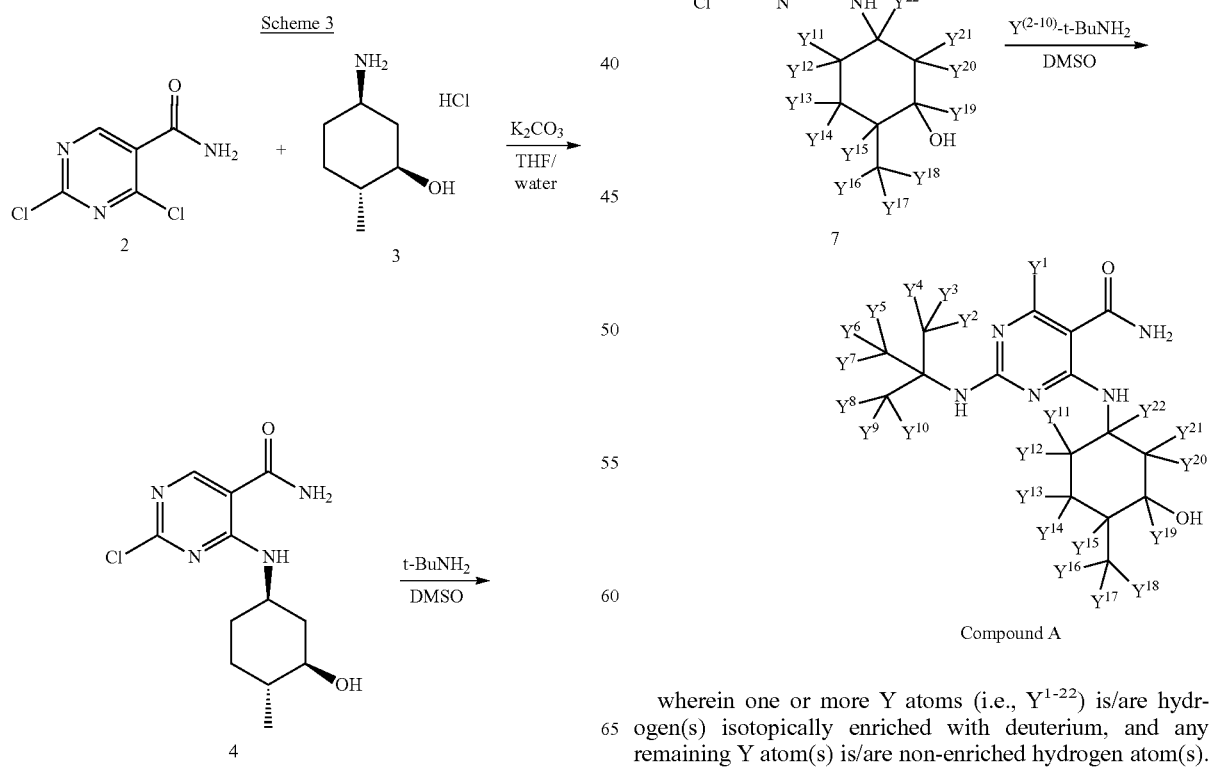

Compound A wherein one or more Y atoms (i.e., $Y^{1-22}$) is/are hydrogen(s) isotopically enriched with deuterium, and any remaining Y atom(s) is/are non-enriched hydrogen atom(s). In particular embodiments, one, two, three, four, five, six, seven, eight, nine or more of the indicated Y atoms is/are isotopically enriched with deuterium, and any remaining Y atom(s) is/are non-enriched hydrogen(s). Isotopically enriched reagents, starting materials, and/or precursors may be obtained commercially or through techniques known to those of skill in the art.

In certain embodiments, the methods of Scheme 4 have the stereochemistry of the following Scheme 5:

Scheme 5

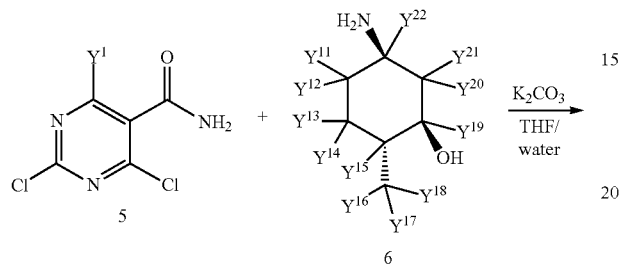

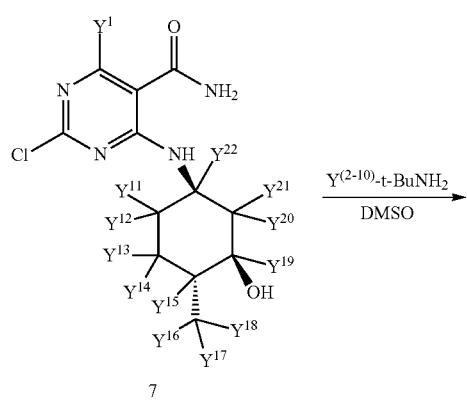

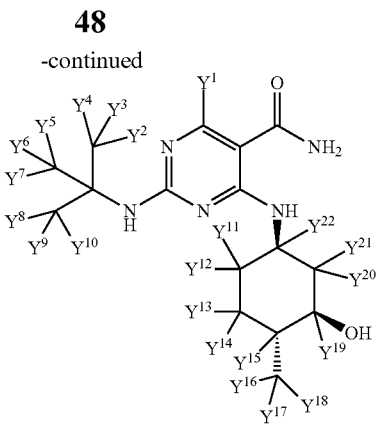

Compound A wherein one or more Y atoms (i.e., $Y^{1-22}$) is/are hydrogen(s) isotopically enriched with deuterium, and any remaining Y atom(s) is/are non-enriched hydrogen atom(s). In particular embodiments, one, two, three, four, five, six, seven, eight, nine or more of the indicated Y atoms is/are isotopically enriched with deuterium, and any remaining Y atom(s) is/are non-enriched hydrogen(s). Isotopically enriched reagents, starting materials, and/or precursors may be obtained commercially or through techniques known to those of skill in the art.

In certain embodiments, the following isotopically enriched starting materials can be used in the methods described herein to afford additional isotopologues of Compound A.

In certain embodiments, a deuterium-enriched analog of precursor (5) is synthesized, wherein one of the Y atoms (i.e., $Y^1$) is hydrogen(s) isotopically enriched with deuterium, and any remaining Y atom(s) is/are non-enriched hydrogen atom(s). In particular embodiments, one of the indicated Y atoms is/are isotopically enriched with deuterium, and any remaining Y atom(s) is/are non-enriched hydrogen(s). Isotopically enriched reagents, starting materials, and/or precursors may be obtained commercially or through techniques known to those of skill in the art.

Scheme 6

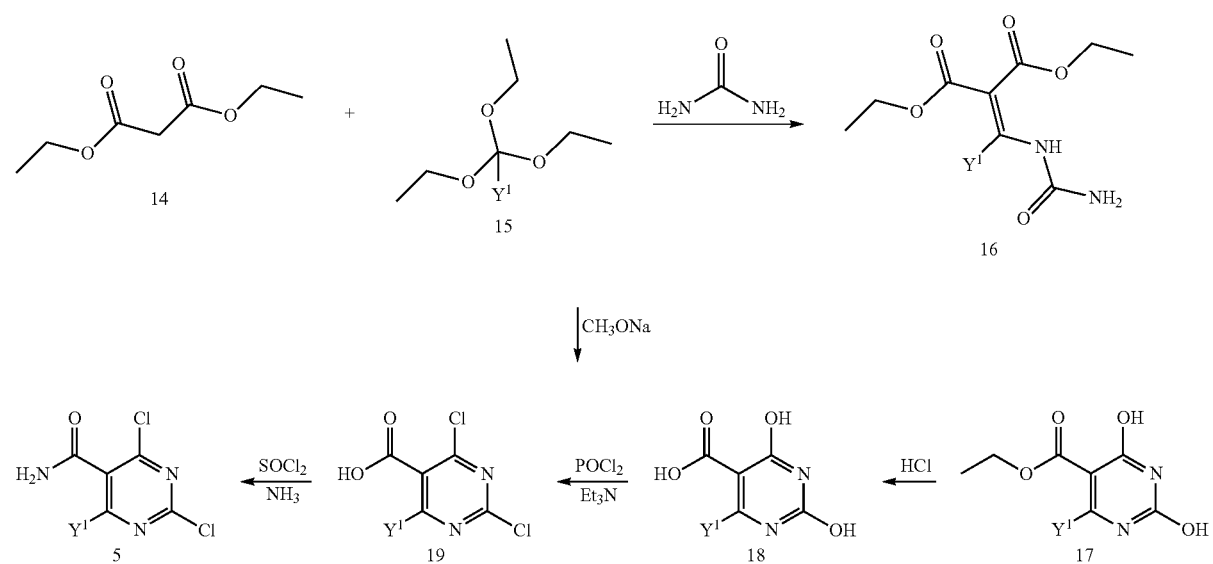

A deuterium-enriched pyrimidine precursor (5) for deuterium-enriched isotopologues of Compound A can be prepared by methods known in the art. For example, as shown in Scheme 6 above, 2,4-dichloropyrimidine-5-carboxamide-$^2$H (5) can be prepared by combining diethyl malonate (14), triethoxymethane-$^2$H (15), and urea to generate diethyl 2-(ureidomethylene)malonate-$^2$H (16). Diethyl 2-(ureidomethylene)malonate-$^2$H (16) is combined with sodium methoxide to afford ethyl 2,4-dihydroxypyrimidine-5-carboxylate-$^2$H (17). Treatment of ethyl 2,4-dihydroxypyrimidine-5-carboxylate-$^2$H (17) with hydrochloric acid followed by halogenation of the resulting 2,4-dihydroxypyrimidine-5-carboxylic acid (18) with phosphoryl chloride and triethylamine affords 2,4-dichloropyrimidine-5-carboxylic acid-$^2$H (19). To a solution of 2,4-dichloropyrimidine-5-carboxylic acid-$^2$H (19) is added thionyl chloride and ammonia to afford the deuterium-enriched precursor 2,4-dichloropyrimidine-5-carboxamide (5), which can be incorporated by the synthesis methods described herein.

In certain embodiments, a deuterium-enriched analog of precursor (6) is synthesized, wherein one or more Y atoms (i.e., $Y^{11-22}$) is/are hydrogen(s) isotopically enriched with deuterium, and any remaining Y atom(s) is/are non-enriched hydrogen atom(s). In particular embodiments, one of the indicated Y atoms is/are isotopically enriched with deuterium, and any remaining Y atom(s) is/are non-enriched hydrogen(s). Isotopically enriched reagents, starting materials, and/or precursors may be obtained commercially or through techniques known to those of skill in the art.

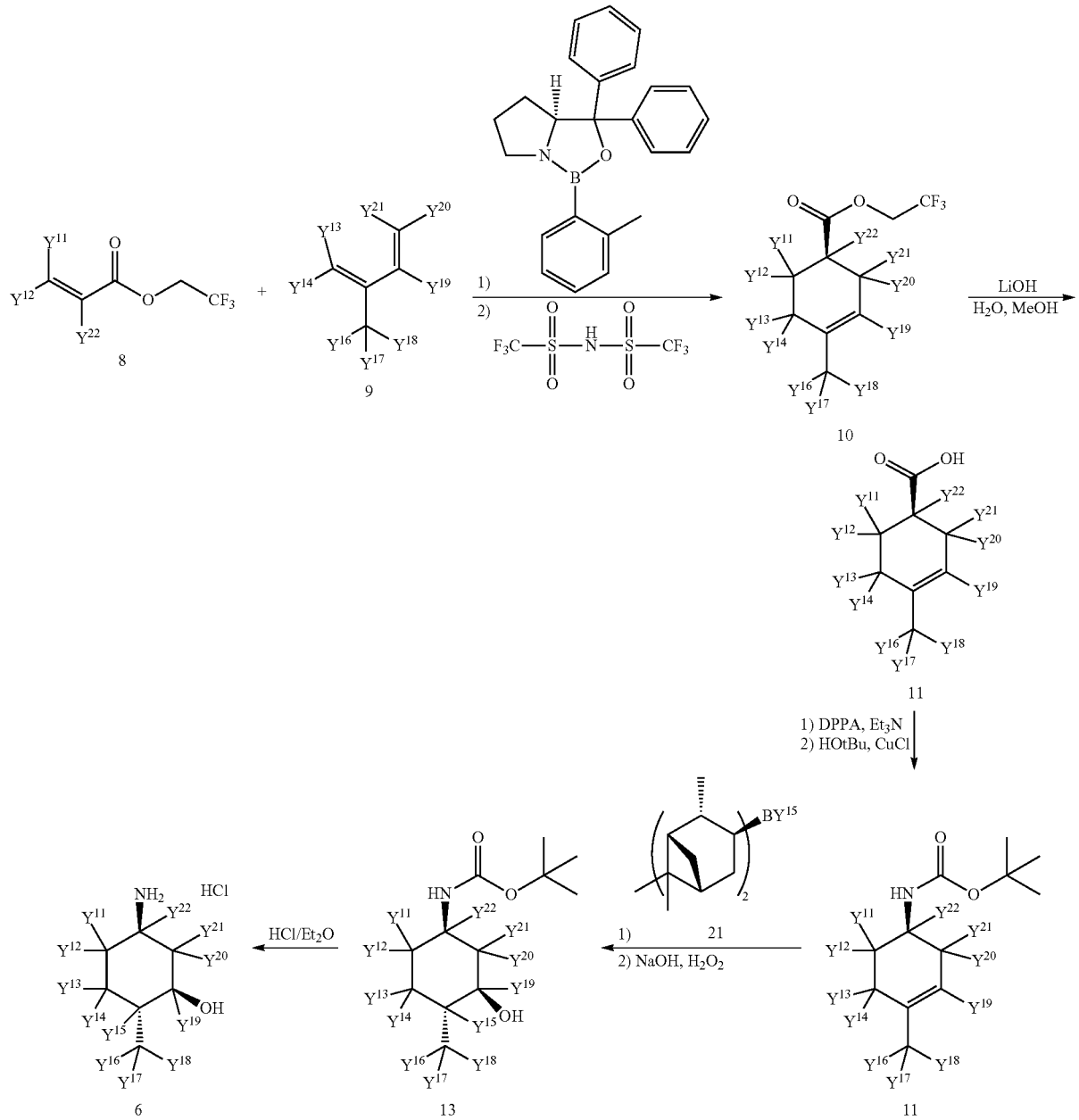

Scheme 7

A deuterium-enriched cyclohexyl precursor (6) for deuterium-enriched isotopologues of Compound A can be prepared by methods known in the art. For example, as shown in Scheme 7 above, (1R,2R,5R)-5-amino-2-methylcyclohexanol hydrochloride-$^2$H (6) can be prepared via an asymmetric Diels-Alder reaction by combining 2,2,2-trifluoroethyl acrylate-$^2$H (8) and isoprene-$^2$H (9) in the presence of borane and sulfonamide catalysts to afford (R)-2,2,2-trifluoroethyl 4-methylcyclohex-3-enecarboxylate-$^2$H (10). A solution of (R)-2,2,2-trifluoroethyl 4-methylcyclohex-3-enecarboxylate-$^2$H (10) in methanol and water is treated with lithium hydroxide to afford (R)-4-methylcyclohex-3-enecarboxylic acid-$^2$H (11) with retention of stereochemistry. Treatment of (R)-4-methylcyclohex-3-enecarboxylic acid-$^2$H (11) with diphenylphosphoryl azide (DPPA) and triethylamine, followed by tert-butoxide and copper chloride, affords (R)-tert-butyl (4-methylcyclohex-3-en-1-Y$^1$)carbamate-$^2$H (12). Hydroboration with diisopinocampheylborane-$^2$H catalyst (21) followed by oxidation of the alkene of (R)-tert-butyl (4-methylcyclohex-3-en-1-Y$^1$)carbamate-$^2$H (12) provides tert-butyl ((1R,3R,4R)-3-hydroxy-4-methylcyclohexyl)carbamate (13). Treatment of tert-butyl ((1R,3R,4R)-3-hydroxy-4-methylcyclohexyl)carbamate (13) with hydrochloric acid affords the deuterium-enriched precursor (1R,2R,5R)-5-amino-2-methylcyclohexanol hydrochloride (6), which can be incorporated by the synthesis methods described herein.

In certain embodiments, partial deuteration of a deuterium-enriched precursor (6) for deuterium-enriched isotopologues of Compound A can be prepared. For example, as shown below in reaction Schemes 8 to 14, (1R,2R,5R)-5-amino-2-methylcyclohexanol hydrochloride-$^2$H (6) can be prepared via an asymmetric Diels-Alder reaction by combining different deuterated or undeuterated combinations of 2,2,2-trifluoroethyl acrylate-$^2$H (8) and isoprene-$^2$H (9) to afford (R)-2,2,2-trifluoroethyl 4-methylcyclohex-3-enecarboxylate-$^2$H (10). Treatment of the resulting (R)-2,2,2-trifluoroethyl 4-methylcyclohex-3-enecarboxylate-$^2$H (10) with different deuterated or undeuterated combinations of diisopinocampheylborane-$^2$H catalyst (21) affords the deuterium-enriched precursor (1R,2R,5R)-5-amino-2-methylcyclohexanol hydrochloride (6), which can be incorporated by the synthesis methods described herein.

Scheme 8

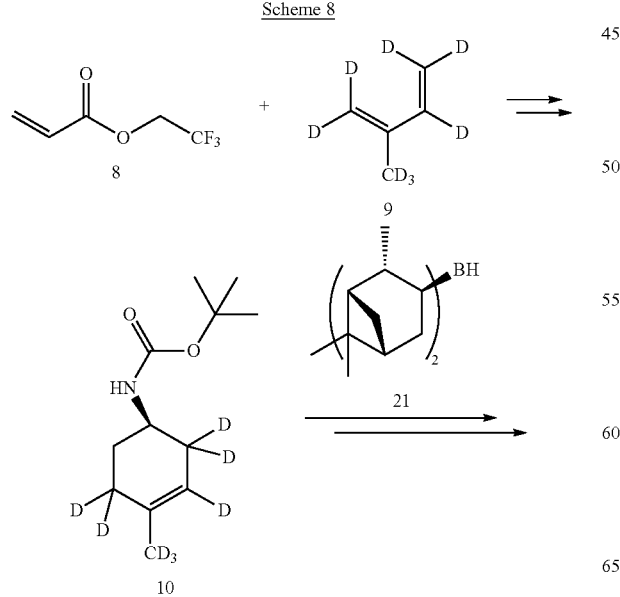

-continued

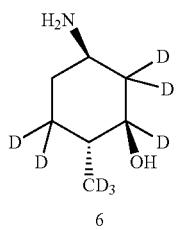

6

Scheme 9

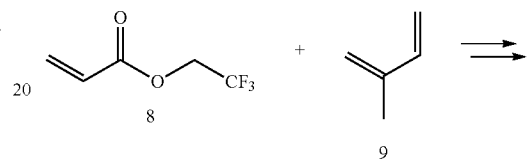

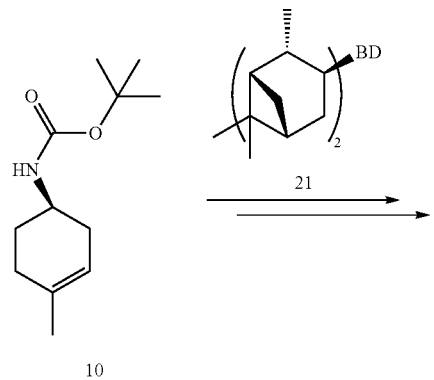

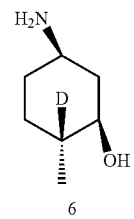

6

Scheme 10

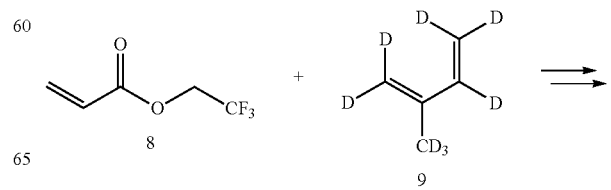

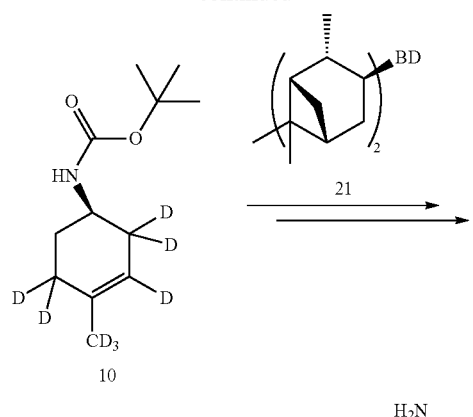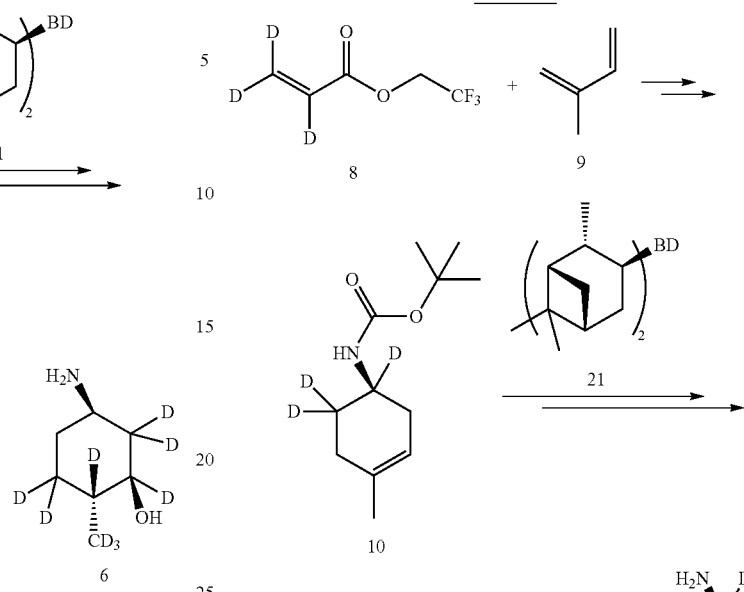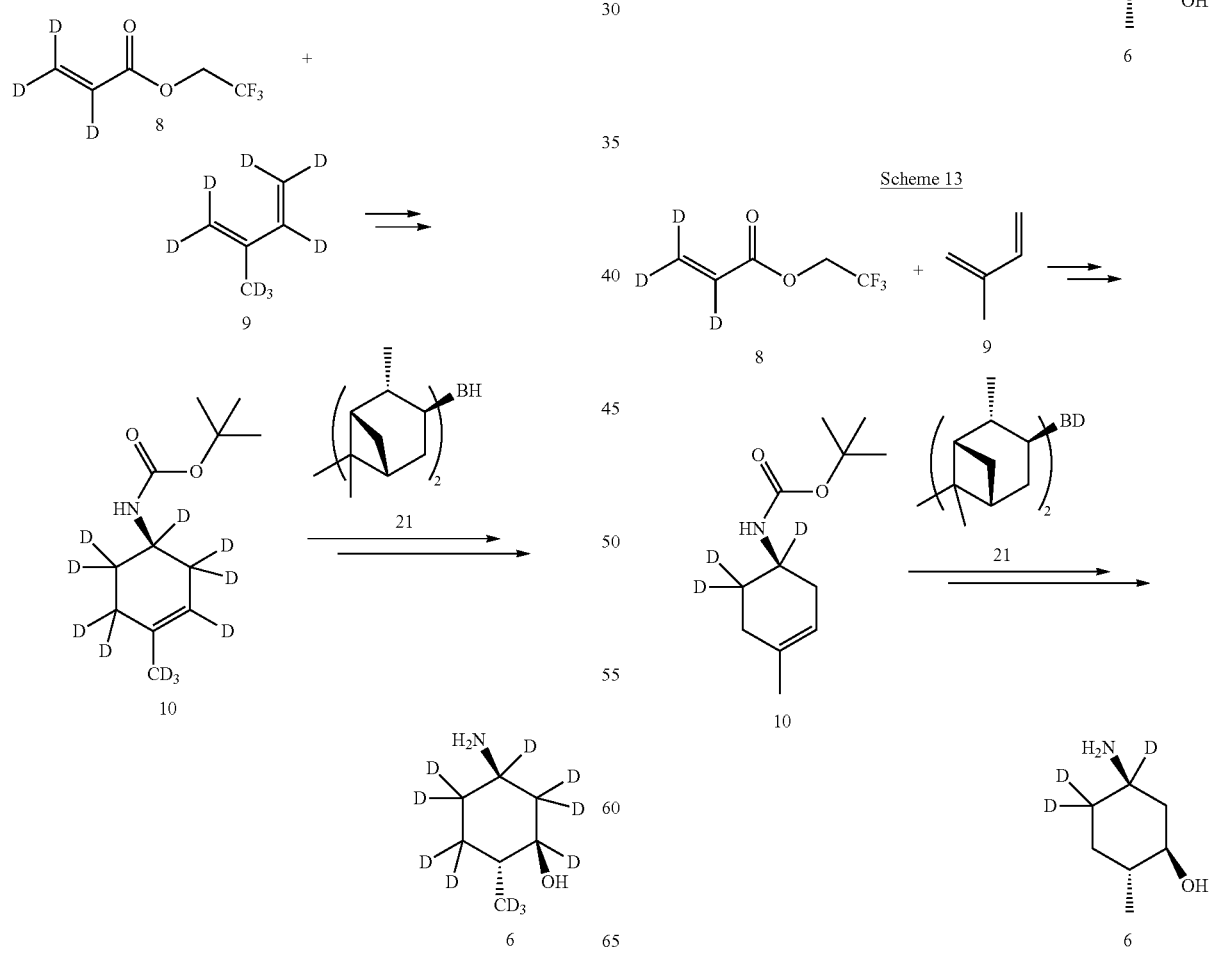

Scheme 14

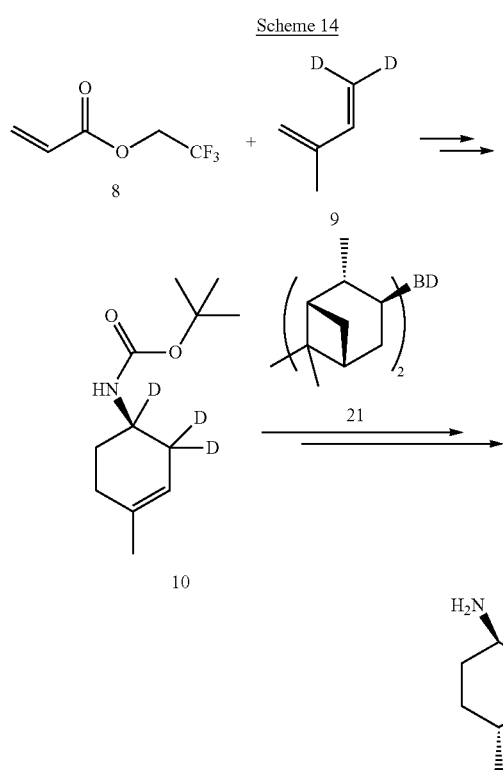

In certain embodiments, a deuterium-enriched acrylate precursor (8) for deuterium-enriched isotopologues of Compound A can be prepared by methods known in the art (*Manufacture of fluoroalkyl (meth)acrylates with high yield in presence of polyphosphoric acid*, Tani, Teruo; Ito, Keisuke; Imamura, Mitsunobu; Kawakami, Naohiko, Jpn. Kokai Tokkyo Koho, 2005225774). For example, as shown in Scheme 15 below, condensation of perdeuterio-acrylic acid (20) with 2,2,2-trifluoroethanol in the presence of polyphosphoric acid provides 2,2,2-trifluoroethyl acrylate $^{2}$H (8).

Scheme 15

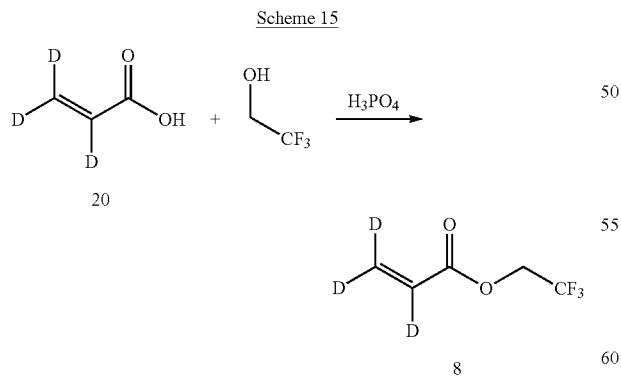

In certain embodiments, one or more hydrogen positions of precursors (8) and (9) of the cyclohexyl portion of Compound A are enriched with deuterium through organic synthesis. For example, a deuterium-enriched precursor (9) for deuterium-enriched isotopologues of Compound A can be prepared by methods known in the art (Craig, David; Regenass, Franz A.; Fowler, Raymond B., *J. of Organic Chemistry*, February 1959, Vol. 24, No. 2, 240-244).

In certain embodiments, partial deuteration of precursor (9) for deuterium-enriched isotopologues of Compound A can be prepared by methods known in the art (Sato, Hisaya; Ono, Akihisha; Tanaka, Yasuyuki, *Polymer*, June 1977, Vol. 18, No. 6, 580-586).

In certain embodiments, diisopinocampheylborane-$^{2}$H catalyst (21) for deuterium-enriched isotopologues of Compound A can be prepared by methods known in the art (Wolfe, Saul; Rauk, Arvi, *Canadian J. of Chemistry*, 1966, Vol. 44, No. 21, 2591-93).

In certain embodiments, partial deuteration of deuterium-enriched isotopologues of Compound A can be prepared. For example, as shown below in reaction Schemes 16 to 24, isotopologues of Compound A can be prepared by combining different deuterated or undeuterated combinations of 2,4-dichloropyrimidine-5-carboxamide-$^{2}$H (5) and (1R,2R,5R)-5-amino-2-methylcyclohexanol hydrochloride-$^{2}$H (6) in the presence of potassium carbonate to afford 2-chloro-4-((3-hydroxy-4-methylcyclohexyl)amino)pyrimidine-5-carboxamide-$^{2}$H (7). Treatment of 2-chloro-4-((3-hydroxy-4-methylcyclohexyl)amino)pyrimidine-5-carboxamide-$^{2}$H (7) with deuterated or undeuterated tert-butyl amine affords a deuterium-enriched isotopologue of Compound A.

Scheme 16

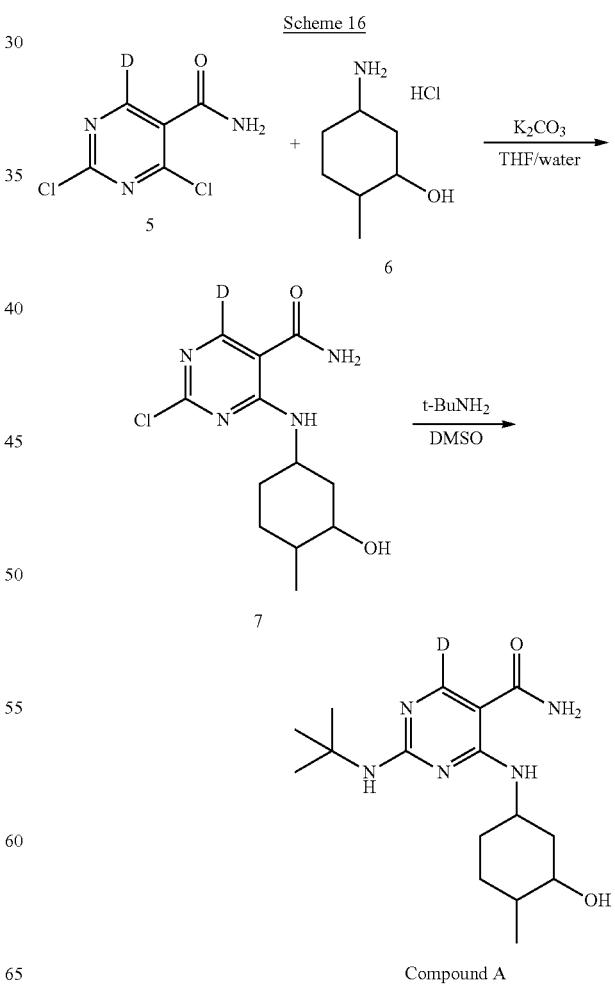

Compound A

Scheme 17
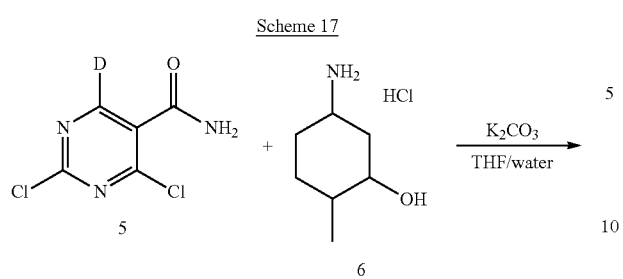
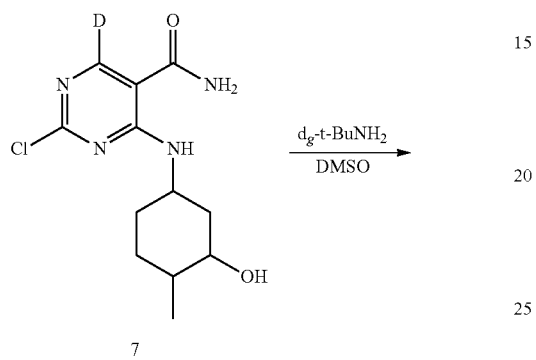
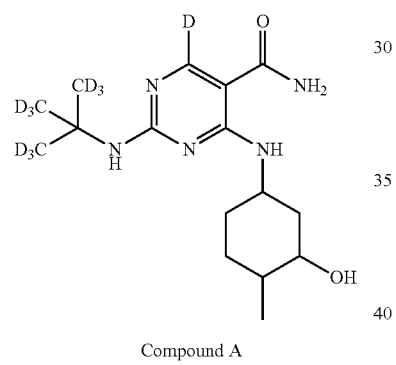
Compound A
Scheme 18
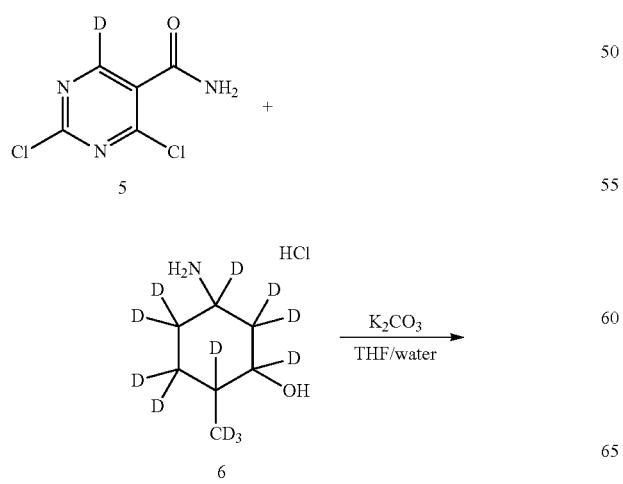
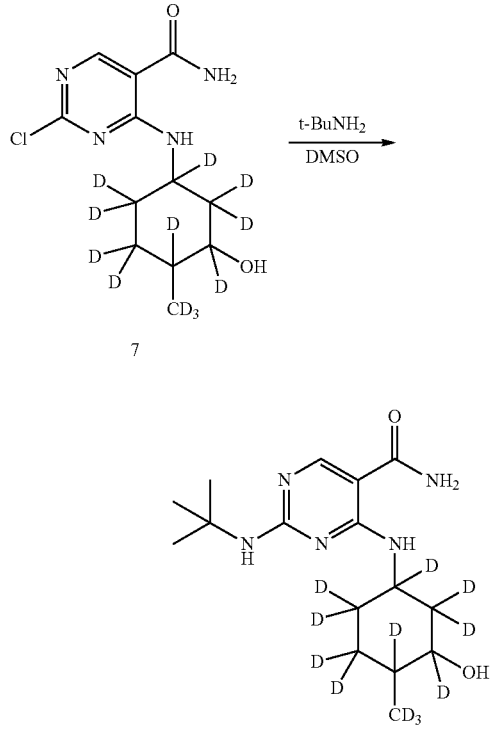
Scheme 19
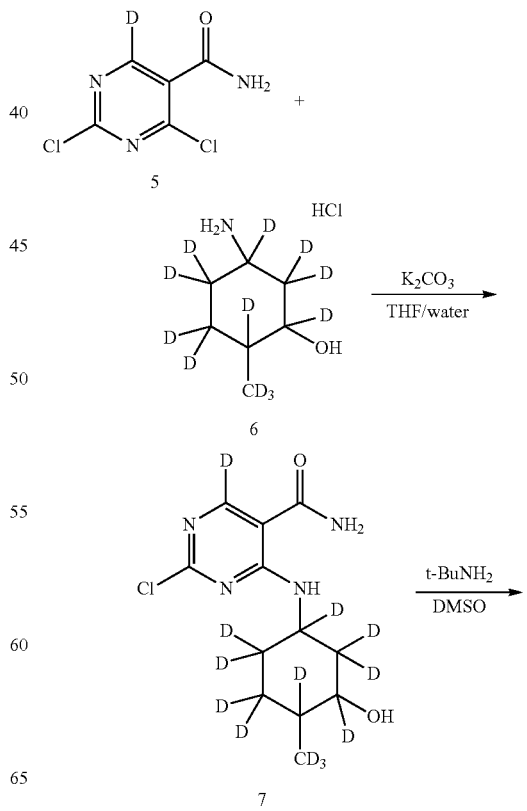

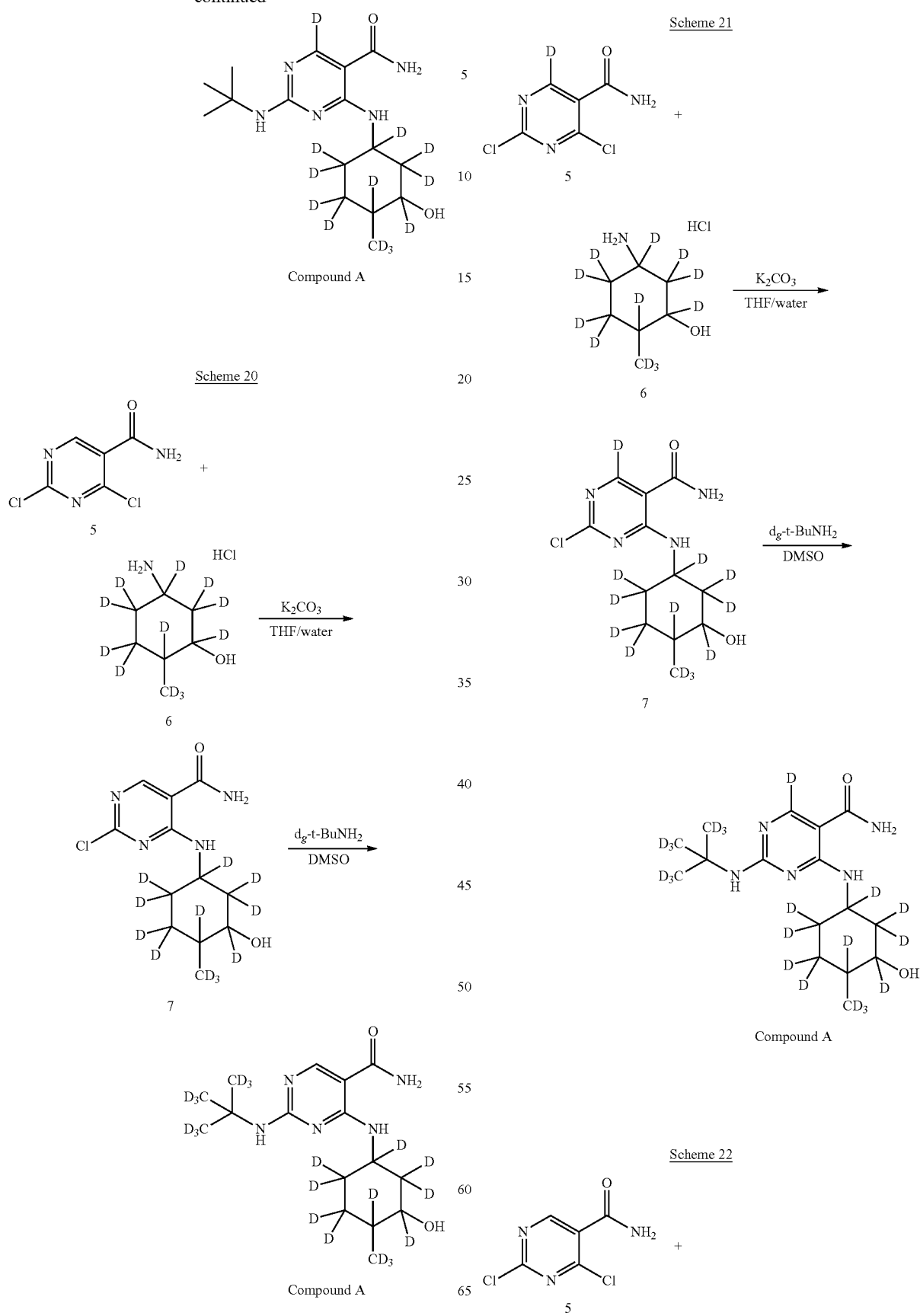

61 -continued
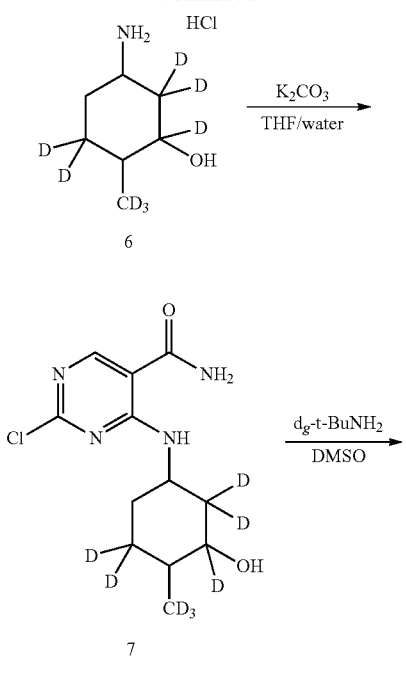
Compound A
Scheme 23
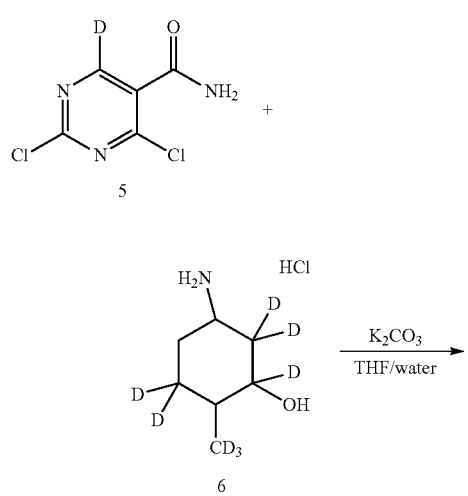
62 -continued
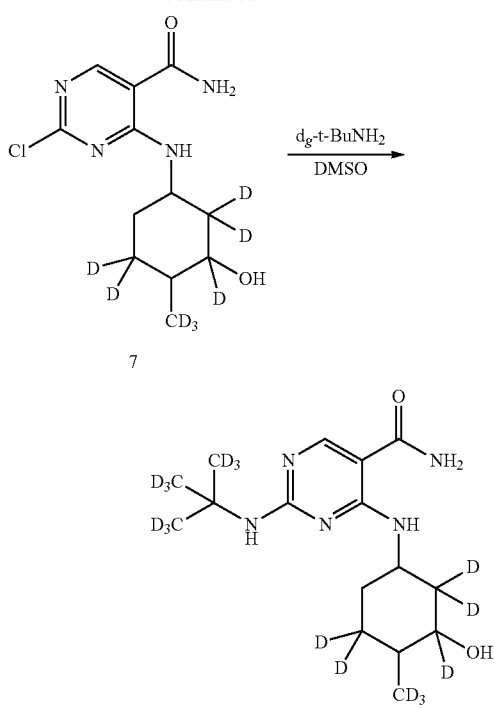
Compound A
Scheme 24
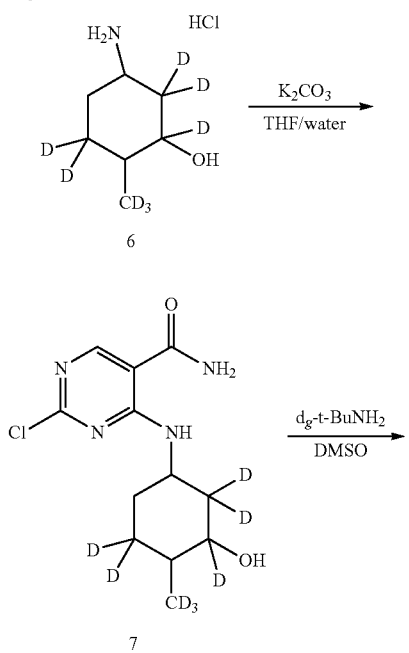

-continued

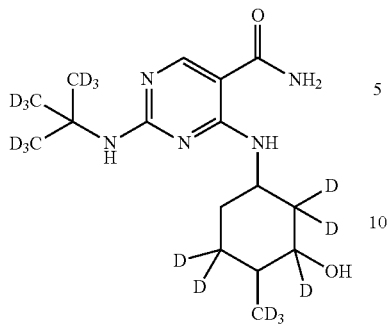

Compound A

In certain embodiments, the methods described in Scheme 1 are employed. In particular embodiments, the methods of Scheme 1 are employed, wherein deuterium-enriched reagents are used, similar to above.

In certain embodiments, one or more hydrogen positions of the pyrimidine portion of Compound A is/are deuterated by subjecting Compound A to conditions suitable for aromatic deuteration, which are known in the art, including for example, those disclosed in the following references, each of which are incorporated herein by reference in their entireties: U.S. Publication No. 2007/0255076; March, J. "Advanced Organic Chemistry, Reactions, Mechanisms, and Structure," Fourth Ed., Wiley, New York, 1992; Larsen et al., *J. Org. Chem.*, 43(18), 3602, 1978; Blake et al., *J. Chem. Soc., Chem Commun.*, 930, 1975; and references cited therein. For example, as depicted in Scheme 25 below, Compound A is treated with $D_2O$ over 5% Pt/C under hydrogen gas to provide an isotopologue of Compound A, as depicted in the scheme above. In certain embodiments, Compound A is converted to a Compound A derivative (e.g., by incorporation of a protecting group), subjected to aromatic deuteration conditions, and converted to deuterium-enriched Compound A.

Scheme 25

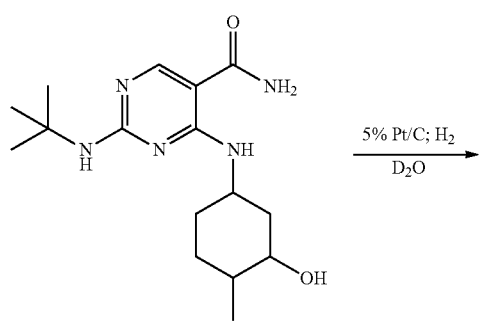

-continued

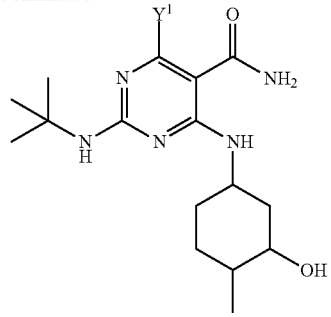

4.3 Methods of Use

Provided herein are methods of treating, preventing, and/or managing various diseases or disorders using isotopologues of Compound A as provided herein, or a pharmaceutically acceptable salt, solvate (e.g., hydrate), prodrug, clathrate, or stereoisomer thereof.

Pharmaceutical compositions and dosage forms of the isotopologues of Compound A have utility as pharmaceuticals to treat, prevent or improve conditions in animals or humans. The isotopologues of Compound A are active against protein kinases, particularly JNK1 and/or JNK2. Accordingly, provided herein are many uses of pharmaceutical compositions and dosage forms of the isotopologues of Compound A, including the treatment or prevention of those diseases set forth below. The methods provided herein comprise the administration of a pharmaceutical composition or dosage form of an isotopologue of Compound A to a subject in need thereof. In one aspect, provided herein are methods of inhibiting a kinase in a cell expressing said kinase, comprising contacting said cell with an effective amount of a pharmaceutical composition or dosage form of an isotopologue of Compound A. In one embodiment, the kinase is JNK1, JNK2, or a mutant or isoform thereof, or a combination thereof.

In another aspect, provided herein are methods for treating or preventing one or more disorders selected from interstitial pulmonary fibrosis, systemic sclerosis, scleroderma, chronic allograft nephropathy, antibody mediated rejection, or lupus, comprising administering to a subject in need thereof an effective amount of a pharmaceutical composition or dosage form of an isotopologue of Compound A. In some such embodiments, the lupus is lupus erythematosus (such as discoid lupus erythematosus, or cutaneous lupus erythematosus) or systemic lupus.

In another aspect, provided herein are methods for treating or preventing liver fibrotic disorders, such as non-alcoholic steatohepatitis, steatosis (i.e. fatty liver), cirrhosis, primary sclerosing cholangitis, primary biliary cirrhosis, hepatitis, hepatocellular carcinoma, and liver fibrosis coincident with chronic or repeated alcohol ingestion (alcoholic hepatitis), with infection (e.g., viral infection such as HCV), with liver transplant, or with drug induced liver injury (e.g., acetaminophen toxicity), comprising administering to a subject in need thereof an effective amount of a pharmaceutical composition or dosage form of an isotopologue of Compound A. In some such aspects, provided herein are methods for treating or preventing diabetes or metabolic syndrome leading to liver fibrotic disorders, such as non-alcoholic steatohepatitis, steatosis (i.e. fatty liver), cirrhosis, primary sclerosing cholangitis, primary biliary cirrhosis, and hepatitis, comprising administering to a subject in need thereof an effective amount of a pharmaceutical composition or dosage form of an isotopologue of Compound A.

In another aspect, provided herein are methods for treating or preventing conditions treatable or preventable by inhibition of JNK1 and/or JNK2, the method comprising administering to a subject in need thereof an effective amount of a pharmaceutical composition or dosage form of an isotopologue of Compound A. Examples of such conditions include rheumatoid arthritis, rheumatoid spondylitis, osteoarthritis, asthma, bronchitis, allergic rhinitis, chronic obstructive pulmonary disease, cystic fibrosis, inflammatory bowel disease, irritable bowel syndrome, mucous colitis, ulcerative colitis, Crohn's disease, Huntington's disease, hepatitis, pancreatitis, nephritis, multiple sclerosis, lupus erythematosus, Type II diabetes, obesity, atherosclerosis, restenosis following angioplasty, left ventricular hypertrophy, myocardial infarction, stroke, ischemic damages of heart, lung, gut, kidney, liver, pancreas, spleen and brain, acute or chronic organ transplant rejection, preservation of the organ for transplantation, organ failure or loss of limb (e.g., including, but not limited to, that resulting from ischemia-reperfusion injury, trauma, gross bodily injury, car accident, crush injury or transplant failure), graft versus host disease, endotoxin shock, multiple organ failure, psoriasis, burn from exposure to fire, chemicals or radiation, eczema, dermatitis, skin graft, ischemia, ischemic conditions associated with surgery or traumatic injury (e.g., vehicle accident, gunshot wound or limb crush), epilepsy, Alzheimer's disease, Parkinson's disease, immunological response to bacterial or viral infection, cachexia, angiogenic and proliferative diseases, solid tumor, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

4.4 Routes of Administrations and Dosage

Pharmaceutical compositions and dosage forms of the isotopologues of Compound A can be administered to a subject orally, topically or parenterally in the conventional form of preparations, such as tablets, granules, powder, troches, pills, suppositories, injections, suspensions, syrups, patches, creams, lotions, ointments, gels, sprays, solutions and emulsions. The effective amount of an isotopologue of Compound A in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of an isotopologue of Compound A to be administered to a subject is rather widely variable and can be subject to the judgment of a healthcare practitioner. In general, an isotopologue of Compound A can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of an isotopologue of Compound A administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of a pharmaceutical composition or dosage form comprising about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of an isotopologue of Compound A to a subject in need thereof.

In another embodiment, provided herein are methods for the treatment or prevention of a disease or disorder comprising the administration of a pharmaceutical composition or dosage form comprising about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day, about 60 mg/day to about 720 mg/day, about 240 mg/day to about 720 mg/day or about 600 mg/day to about 800 mg/day of an isotopologue of Compound A to a subject in need thereof. In a particular embodiment, the methods disclosed herein comprise the administration of a pharmaceutical composition or dosage form comprising about 400 mg/day, about 600 mg/day or about 800 mg/day of an isotopologue of Compound A to a subject in need thereof.

In another embodiment, provided herein are methods for the treatment or prevention of a disease or disorder comprising the administration of a pharmaceutical composition or dosage form comprising about 10 mg/day to about 720 mg/day, about 10 mg/day to about 480 mg/day, about 60 mg/day to about 720 mg/day or about 240 mg/day to about 720 mg/day of an isotopologue of Compound A to a subject in need thereof. In one embodiment, provided herein are methods for the treatment or prevention of a disease or disorder comprising the administration of a pharmaceutical composition or dosage form comprising about 60 mg/day, about 160 mg/day, or about 400 mg/day of an isotopologue of Compound A to a subject in need thereof. In another embodiment, provided herein are methods for the treatment or prevention of a disease or disorder comprising the administration of a pharmaceutical composition or dosage form comprising about 200 mg/day of an isotopologue of Compound A to a subject in need thereof.

In one embodiment, provided herein are methods for the treatment or prevention of a disease or disorder comprising the administration of a pharmaceutical composition, or dosage form comprising about 10 mg/day, about 30 mg/day, about 60 mg/day, about 120 mg/day, about 240 mg/day, about 480 mg/day, or about 720 mg/day of Compound A to a subject in need thereof. In one embodiment, provided herein are methods for the treatment or prevention of a disease or disorder comprising the administration of a pharmaceutical composition, or dosage form comprising about 60 mg/day, about 160 mg/day, or about 400 mg/day of Compound A to a subject in need thereof. In another embodiment, provided herein are methods for the treatment or prevention of a disease or disorder comprising the administration of a pharmaceutical composition, or dosage form comprising about 200 mg/day of Compound A to a subject in need thereof. In one embodiment, provided herein are methods for the treatment or prevention of a disease or disorder comprising the administration of a pharmaceutical composition, or dosage form comprising about 10 mg/day, about 30 mg/day, about 60 mg/day, about 120 mg/day, about 160 mg/day, about 200 mg/day, about 240 mg/day, about 400 mg/day, about 480 mg/day, or about 720 mg/day of Compound A to a subject in need thereof.

In another embodiment, provided herein are unit dosage formulations that comprise between about 10 mg and about 100 mg, about 1 mg and about 200 mg, about 30 mg and about 200 mg, about 35 mg and about 1400 mg, about 125 mg and about 1000 mg, about 250 mg and about 1000 mg, or about 500 mg and about 1000 mg of an isotopologue of Compound A.

In another embodiment, provided herein are unit dosage formulations that comprise about 1 mg, about 5 mg, about 10 mg, about 15 mg, about 20 mg, about 30 mg, about 35 mg, about 50 mg, about 60 mg, about 70 mg, about 100 mg, about 120 mg, about 125 mg, about 140 mg, about 175 mg, about 200 mg, about 240 mg, about 250 mg, about 280 mg, about 350 mg, about 480 mg, about 500 mg, about 560 mg, about 700 mg, about 720 mg, about 750 mg, about 1000 mg or about 1400 mg of an isotopologue of Compound A.

In another embodiment, provided herein are unit dosage formulations that comprise about 30 mg, about 100 mg or about 200 mg of an isotopologue of Compound A.

Pharmaceutical compositions and dosage forms of an isotopologue of Compound A can be administered once, twice, three, four or more times daily. In one embodiment, pharmaceutical compositions and dosage forms of an isotopologue of Compound A can be administered once daily for 14 days.

Pharmaceutical compositions and dosage forms of an isotopologue of Compound A can be administered orally for reasons of convenience. In one embodiment, when administered orally, pharmaceutical compositions and dosage forms of the isotopologues of Compound A are administered with a meal and water. In another embodiment, pharmaceutical compositions and dosage forms of the isotopologues of Compound A (e.g., granules or dispersible tablets) are dispersed in water or juice (e.g., apple juice or orange juice) and administered orally as a suspension.

Pharmaceutical compositions and dosage forms of the isotopologues of Compound A can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

4.5 Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent.

In some embodiments, the active ingredients and excipients are directly blended and compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and compressed to tablets, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

In certain embodiments, provided herein are methods for preparing a composition provided herein, comprising: (i) weighing out the desired amount of an isotopologue of Compound A and the desired amount of a first portion of excipients; (ii) preparing an aqueous solution of surfactant(s); (iii) passing the mixture of an isotopologue of Compound A and the first portion of the excipients without the surfactant(s) through a screen; (iv) mixing or blending an isotopologue of Compound A, the aqueous solution of surfactant(s) and the first portion of the excipients; (v) drying the mixture; (vi) passing a second portion of the excipients through a screen; (vii) mixing or blending the mixture of step (v) and the second portion of the excipients; (viii) weighing out the desired amount of lubricating agents; (ix) passing the lubricating agents through a screen; (x) mixing or blending the mixture of step (vii) and the lubricating agents; (xi) compressing the mixture of step (x); and (ix) coating the compressed mixture with a coating agent. In one embodiment, the mixture of an isotopologue of Compound A, the excipients and the lubricating agents is compressed into a tablet form. In one embodiment, the screen is 18 mesh screen. In another embodiment, the screen is 1000 µm screen. In one embodiment, the screen is 20 mesh screen. In another embodiment, the screen is 841 µm screen. In one

5 EXAMPLES

General: Isotopically enriched analogs of the compounds provided herein may generally be prepared according known procedures for the synthesis of Compound A, wherein one or more of the reagents, starting materials, precursors, or intermediates used is replaced by one or more isotopically enriched reagents, starting materials, precursors, or intermediates. Isotopically enriched reagents, starting materials, precursors, or intermediates are commercially available or may be prepared by routine procedures known to one of skill in the art. Schemes for the preparation of exemplary isotopically enriched compounds are illustrated below.

ABBREVIATIONS

AcOH: acetic acid
AP: area purity
CP: chemical purity
DCM: dichloromethane
DIEA: diisopropylamine
DPPA: diphenylphosphoryl azide
DMSO: dimethylsulfoxide
EDC: 1-ethyl-3-(3-dimethylaminopropyl) carbodiimide
EtOAc: ethyl acetate
EtOH: ethanol
$H_2$: hydrogen gas
$H^2$: deuterium
HOtBu: tert-butoxide
HPLC: high performance liquid chromatography
i-PrOH: isopropanol
LC-MS: liquid chromatography/mass spectrometry
MeCN: acetonitrile
MeOH: methanol
MTBE: methyl tert-butyl ether
NMR: nuclear magnetic resonance
PMA: phosphomolybdic acid
Pt/C: platinum on carbon
RCP: radiochemical purity
RT: retention time
TEA: triethylamine
TFA: trifluoroacetic acid
THF: tetrahydrofuran
TLC: thin layer chromatography
Trt: trityl

5.1 Example 1

4-{[(1R,3R,4R)-3-hydroxy-4-methylcyclohexyl]amino}-2-{[2-(2H3)methyl(2H6)propan-2-yl]amino}pyrimidine-5-carboxamide (Compound A): As depicted in Scheme 26 below, a mixture of precursor (7) (1.6 g) and t-butyl-$d_9$-amine (4.95 mL) in DMSO (8 mL) was heated at 65° C. for 91 hours. The mixture was cooled to 60° C. Water (8 mL) was charged while maintaining the batch temperature at 60° C. After 2.5 hours at 60° C., water (24 mL) was charged while maintaining the batch temperature at 60° C. After 2 hours at 60° C., the batch was cooled to 25° C. and kept for 11 hours. The solids was filtered and washed with water. The solids was dried in a vacuum oven at 40° C. with nitrogen bleed to give 4-{[(1R,3R,4R)-3-hydroxy-4-methylcyclohexyl]amino}-2-{[2-(2H3)methyl(2H6)propan-2-Y$^1$]amino}pyrimidine-5-carboxamide (Compound A) (1.72 g). $^1$H NMR (DMSO-$d_6$, 300 MHz): δ 0.94 (d, J=6.4 Hz, 3H), 0.96-1.04 (m, 1H), 1.04-1.33 (m, 3H), 1.67 (dd, J=3.3, 13.1 Hz, 1H), 1.89 (d, J=11.0 Hz, 1H), 2.12 (d, J=11.1 Hz, 1H), 2.85-3.06 (m, 1H), 3.71-4.03 (m, 1H), 4.55 (dd, J=2.1, 5.5 Hz, 1H), 6.59 (br. s., 1H), 6.73-8.01 (m, 2H), 8.34 (s, 1H), 8.93 (br. s., 1H).

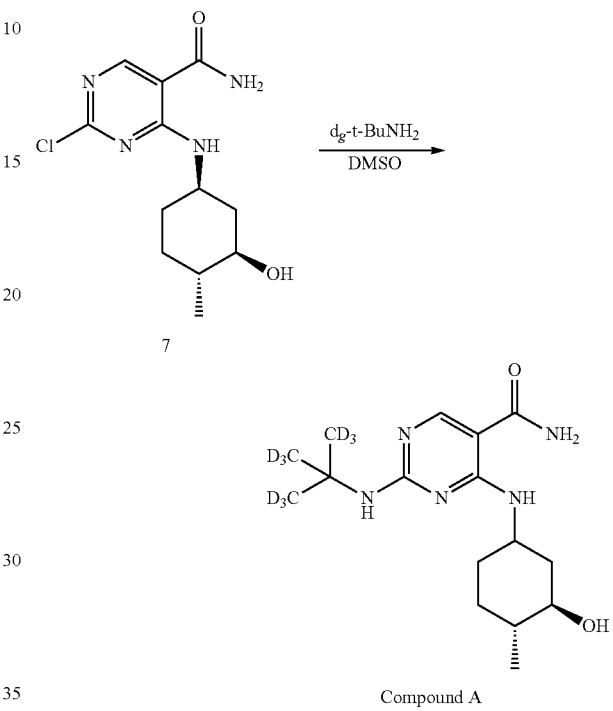

Scheme 26

5.2 Determination of Isotopic Enrichment

Isotopic enrichment may be confirmed and quantified by mass spectrometry and/or NMR, including, for example, proton-NMR; carbon-13 NMR; or nitrogen-15 NMR.

Isotopic enrichment may also be confirmed by single-crystal neutron diffraction. For example, the isotopic ratio at a particular hydrogen/deuterium position in a deuterated Compound A can be determined using single-crystal neutron diffraction. Neutron diffraction is advantageous because neutrons are scattered by the nucleus of an atom, therefore allowing for discrimination between isotopes, such as hydrogen and deuterium, which differ in the number of neutrons in the nucleus.

A single crystal of suitable size and quality comprising the deuterated Compound A is grown using standard methods of crystal growth. For single-crystal neutron diffraction experiments, crystals of several cubic millimeters are generally required for suitable data collection. A minimum size for a single crystal is typically about 1 cubic millimeter. Suitable single crystals are obtained by dissolving the deuterated Compound A in a solvent with appreciable solubility, then slowly evaporating or cooling the solution to yield crystals of suitable size and quality. Alternatively, suitable single crystals are obtained by dissolving the deuterated Compound A in a solvent with appreciable solubility, then slowly diffusing into the solution of antisolvent (i.e., a solvent in which the deuterated Compound A is not appreciably soluble) to yield crystals of suitable size and quality. These In another embodiment, the screen is 30 mesh screen. In another embodiment, the screen is 595 μm screen.

and other suitable methods of crystal growth are known in the art and are described, e.g., in George H. Stout & Lyle H. Jensen, X-Ray Structure Determination: A Practical Guide 74-92 (John Wiley & Sons, Inc. 2nd ed. 1989) (the entirety of which is incorporated herein).

After isolating a suitable single crystal comprising the deuterated Compound A, the crystal is mounted in a neutron beam, neutron diffraction data is collected, and the crystal structure is solved and refined. Different neutron sources can be used, including steady-state sources and pulsed spallation sources. Examples of steady-state sources include the Grenoble ILL High Flux Reactor (Grenoble, France) and the Oak Ridge High Flux Isotope Reactor (Oak Ridge, Tenn.). Examples of pulsed spallation sources include ISIS, the spallation neutron source at Rutherford Appleton Laboratory (Oxfordshire, UK); the Intense Pulsed Neutron Source (IPNS) at Argonne National Laboratory (Argonne, Ill.), the Los Alamos Neutron Science Center (LANSCE) at Los Alamos National Laboratory (Los Alamos, N. Mex.), and the Neutron Science Laboratory (KENS) at KEK (Tsukuba, Ibaraki, Japan).

For a steady-state neutron source, four-circle diffractometer techniques are used with a monochromatic beam and a single detector, rotating the crystal and detector to measure each reflection sequentially. Diffractometer control software and step-scanning methods for intensity extraction can be adopted from routine four-circle X-ray diffractometry methods. One or more area detectors, including area detector arrays, may alternatively be used to increase the region of reciprocal space accessed in a single measurement. A broad band (white) beam used with an area detector allows for Laue or quasi-Laue diffraction with a stationary crystal and detector.

For a pulse source with a white neutron beam, time-of-flight Laue diffraction techniques are used, which allow for the determination of the velocity, energy, and wavelength of each neutron detected. This approach combines wavelength sorting with large area position-sensitive detectors, and allows for fixed scattering geometries (i.e., a stationary crystal and detector). Pulse source data collected in this fashion allows for rapid collection of data sets and good accuracy and precision in standard structural refinements. Additional details regarding steady-state and pulse source neutron diffraction experiments are well known in the art. See, e.g., Chick C. Wilson, Neutron Single Crystal Diffraction, 220 Z. Kristallogr. 385-98 (2005) (incorporated by reference herein in its entirety).

Crystal structure data, including particular isotopic ratios, are obtained from neutron diffraction data following routine structure solution and refinement processes. Structure solution is carried out using one of several methods, including direct methods and Patterson methods. For convenience, atomic coordinates from prior single crystal X-ray diffraction experiments may be used as a starting point for structure refinement using neutron diffraction data; this approach permits additional refinement of atomic positions, including hydrogen and deuterium positions. Refinement is conducted using full-matrix least-squares methods to achieve optimal agreement between the observed diffraction intensities and those calculated from the structural model. Ideally, full anisotropic refinement is carried out on all atoms, including the H/D atomic positions of interest. Data collection, structure solution and structure refinement methods, both for X-ray and neutron diffraction data, are well known in the art. See, e.g., Chick C. Wilson, Single Crystal Neutron Diffraction from Molecular Materials (World Scientific Publishing Co. 2000); George H. Stout & Lyle H. Jensen, X-Ray Structure Determination: A Practical Guide (John Wiley & Sons, Inc. 2nd ed. 1989) (both of which are incorporated herein in their entireties).

The isotopic ratio for a particular position on a deuterated Compound A is calculated by examining the neutron scattering cross sections for the H/D atomic position of interest. The scattering cross section is obtained as part of the refinement process discussed above. An example of determining the isotopic ratio for a partially deuterated compound is provided by G. A. Jeffrey et al., Neutron Diffraction Refinement of Partially Deuterated β-D-Arabinopyranose and α-L-Xylopyranose at 123 K, B36 Acta Crystallographica 373-77 (1980) (incorporated by reference herein in its entirety). Jeffrey et al. used single-crystal neutron diffraction to determine the percentage deuterium substitution for hydroxyl groups on two sugar compounds of interest. Employing the methods discussed by Jeffrey et al., one may similarly ascertain the isotopic ratio for a particular H/D position on a deuterated Compound A.

All of the cited references are incorporated herein by reference in their entirety.

What is claimed is:

1. A method for treating a disease selected from a group consisting of systemic sclerosis, scleroderma, chronic allograft nephropathy, antibody mediated rejection, and lupus, comprising administering to a subject having the disease an effective amount of a compound having the following structure:

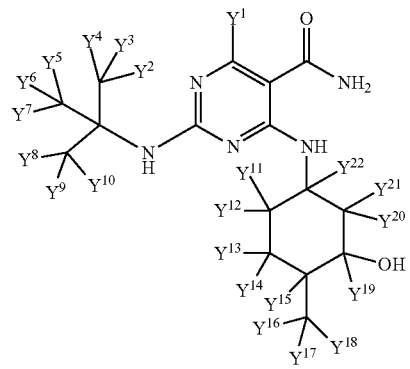

or a pharmaceutically acceptable salt, stereoisomer or solvate thereof, wherein one or more of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ is a hydrogen that is isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ are non-enriched hydrogen atoms.

2. The method of claim 1, wherein the compound has the following structure:

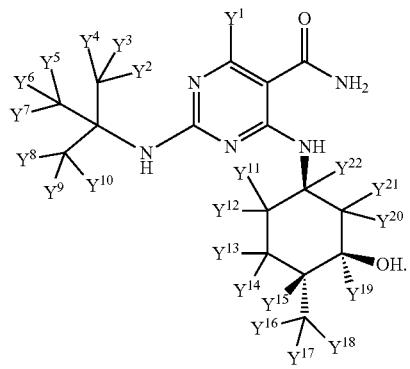

3. The method of claim 1, wherein one of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ is isotopically enriched with deuterium, and the others are non-enriched hydrogens.

4. The method of claim 1, wherein two of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ are isotopically enriched with deuterium, and the others are non-enriched hydrogens.

5. The method of claim 1, wherein the compound is:

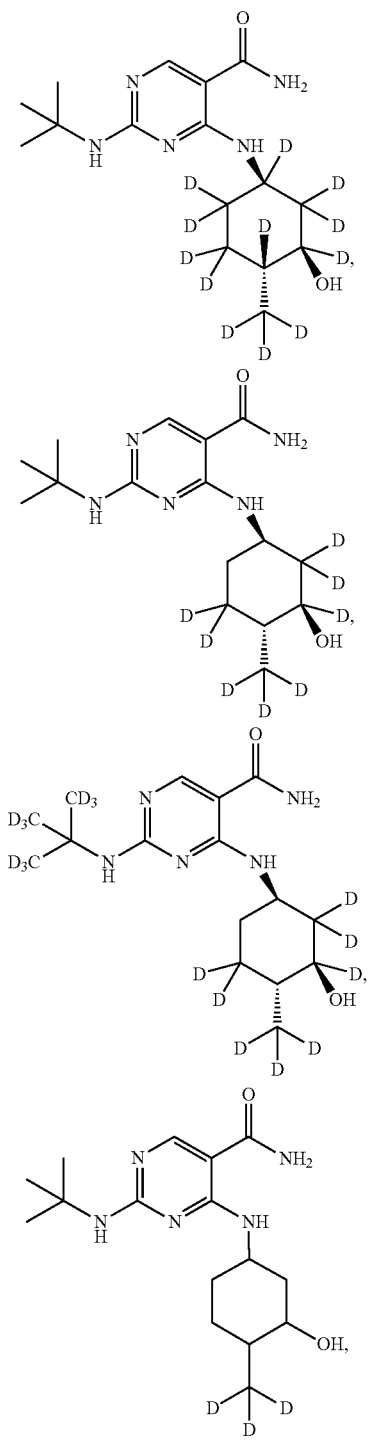

-continued

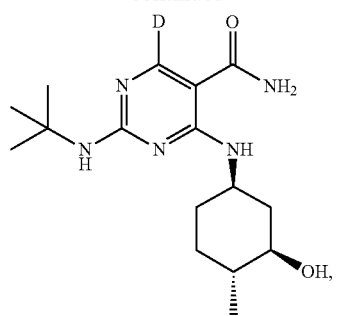

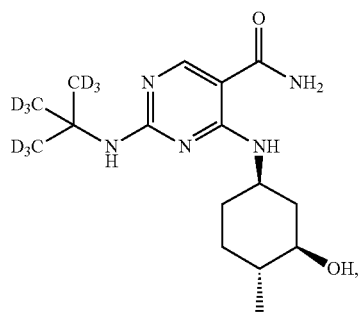

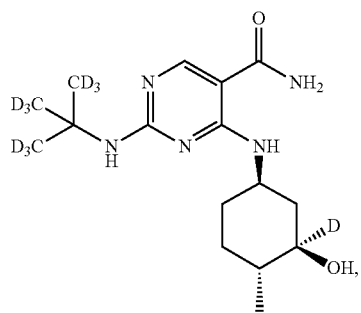

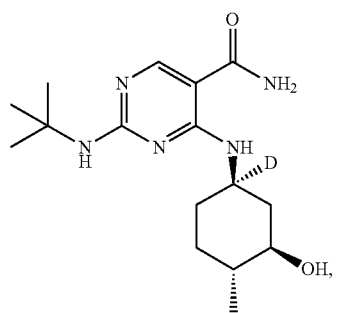

-continued

[Chemical structure: pyrimidine-5-carboxamide with 2-[(1,1,1,3,3,3-hexadeutero-2-(trideuteromethyl)propan-2-yl)amino] substituent and 4-[(3-hydroxy-3-deutero-4-methylcyclohexyl)amino] substituent], or

[Chemical structure: pyrimidine-5-carboxamide with 2-(tert-butylamino) substituent and 4-[(3-hydroxy-3-deutero-4-methylcyclohexyl)amino] substituent]

6. The method of claim 1, wherein the compound is:

[Chemical structure: pyrimidine-5-carboxamide with 2-[(1,1,1,3,3,3-hexadeutero-2-(trideuteromethyl)propan-2-yl)amino] substituent and 4-[(3-hydroxy-4-methylcyclohexyl)amino] substituent]

7. The method of claim 1, wherein the compound at a concentration of 10 μM inhibits JNK1 by at least about 50%.

8. The method of claim 1, wherein the disease is systemic sclerosis.

9. The method of claim 1, wherein the disease is scleroderma.

10. The method of claim 1, wherein the disease is chronic allograft nephropathy.

11. The method of claim 1, wherein the disease is antibody mediated rejection.

12. The method of claim 1, wherein the disease is lupus.

* * * * *